(12) United States Patent
Kaib et al.

(10) Patent No.: US 10,155,118 B2
(45) Date of Patent: Dec. 18, 2018

(54) SYSTEMS AND METHODS FOR UTILIZING IDENTIFICATION DEVICES IN A WEARABLE MEDICAL THERAPY DEVICE

(71) Applicant: ZOLL Medical Corporation, Chelmsford, MA (US)

(72) Inventors: Thomas E. Kaib, North Huntingdon, PA (US); John Macho, Pittsburgh, PA (US); Shane Volpe, Saltsburg, PA (US); Phillip Amsler, Oakmont, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 15 days.

(21) Appl. No.: 14/448,761

(22) Filed: Jul. 31, 2014

(65) Prior Publication Data

US 2015/0035654 A1 Feb. 5, 2015

Related U.S. Application Data

(60) Provisional application No. 61/861,110, filed on Aug. 1, 2013, provisional application No. 62/021,609, filed
(Continued)

(51) Int. Cl.
| | |
|---|---|
| *A61N 1/39* | (2006.01) |
| *H01M 2/10* | (2006.01) |
| *A61B 90/90* | (2016.01) |
| *A61B 90/98* | (2016.01) |
| *H01M 10/48* | (2006.01) |

(52) U.S. Cl.
CPC ............ *A61N 1/3925* (2013.01); *A61B 90/98* (2016.02); *A61N 1/3987* (2013.01); *H01M 2/1022* (2013.01); *H01M 10/48* (2013.01); *A61B 90/90* (2016.02); *A61N 1/3968* (2013.01); *A61N 1/3975* (2013.01); *H01M 2220/30* (2013.01)

(58) Field of Classification Search
USPC ....................................................... 340/10.51
See application file for complete search history.

(56) References Cited

U.S. PATENT DOCUMENTS

| | | | |
|---|---|---|---|
| 4,928,690 A | 5/1990 | Heilman et al. | |
| 5,078,134 A | 1/1992 | Heilman et al. | |
(Continued)

FOREIGN PATENT DOCUMENTS

| | | |
|---|---|---|
| WO | 2004084720 A2 | 10/2004 |
| WO | 2007114968 A2 | 10/2007 |
| WO | 2008054980 A2 | 5/2008 |

*Primary Examiner* — Thomas S McCormack
(74) *Attorney, Agent, or Firm* — The Webb Law Firm

(57) ABSTRACT

A system includes: at least one identification device associated with a wearable medical therapy device and configured to have information read therefrom and written thereto; at least one controller operatively connected to the at least one identification device and configured to at least one of retrieve the information from the at least one identification device and write the information to the at least one identification device; and at least one device positioned externally from the wearable medical therapy device and configured to interrogate the at least one identification device to at least one of obtain the information from the at least one identification device and write additional information to the at least one identification device.

17 Claims, 22 Drawing Sheets

Related U.S. Application Data on Jul. 7, 2014, provisional application No. 62/025,660, filed on Jul. 17, 2014.

(56) References Cited

U.S. PATENT DOCUMENTS

| | | | |
|---|---|---|---|
| 5,466,244 A | 11/1995 | Morgan | |
| 5,503,158 A | 4/1996 | Coppock et al. | |
| 5,662,690 A | 9/1997 | Cole et al. | |
| 5,716,380 A | 2/1998 | Yerkovich et al. | |
| 5,724,025 A | 3/1998 | Tavori | |
| 5,730,143 A | 3/1998 | Schwarzberg | |
| 5,741,306 A | 4/1998 | Glegyak et al. | |
| 5,749,913 A | 5/1998 | Cole | |
| 5,772,586 A | 6/1998 | Heinonen et al. | |
| 5,782,878 A | 7/1998 | Morgan et al. | |
| 5,879,374 A | 3/1999 | Powers et al. | |
| 5,899,925 A | 5/1999 | Ochs et al. | |
| 5,919,212 A | 7/1999 | Olson et al. | |
| 5,931,791 A | 8/1999 | Saltzstein et al. | |
| 5,941,829 A | 8/1999 | Saltzstein et al. | |
| 5,944,669 A | 8/1999 | Kaib | |
| 5,955,956 A | 9/1999 | Stendahl et al. | |
| 5,983,137 A | 11/1999 | Yerkovich | |
| 6,065,154 A | 5/2000 | Hulings et al. | |
| 6,169,387 B1 | 1/2001 | Kaib | |
| 6,253,099 B1 | 6/2001 | Oskin et al. | |
| 6,280,461 B1 | 8/2001 | Glegyak et al. | |
| 6,314,320 B1 | 11/2001 | Powers et al. | |
| 6,364,834 B1 | 4/2002 | Reuss et al. | |
| 6,366,809 B1 | 4/2002 | Olson et al. | |
| 6,397,104 B1 | 5/2002 | Miller et al. | |
| 6,405,082 B1 | 6/2002 | Borgenicht | |
| 6,449,504 B1 | 9/2002 | Conley et al. | |
| 6,456,042 B1 | 9/2002 | Kwok | |
| 6,494,829 B1 | 12/2002 | New, Jr. et al. | |
| 6,498,951 B1 | 12/2002 | Larson et al. | |
| 6,510,344 B1 | 1/2003 | Halpern | |
| 6,537,214 B1 | 3/2003 | Hood et al. | |
| 6,553,262 B1 | 4/2003 | Lang et al. | |
| 6,569,095 B2 | 5/2003 | Eggers | |
| 6,591,135 B2 | 7/2003 | Palmer et al. | |
| 6,597,948 B1 | 7/2003 | Rockwell et al. | |
| 6,658,296 B1 | 12/2003 | Wong et al. | |
| 6,662,046 B2 | 12/2003 | Hansen | |
| 6,664,891 B2 | 12/2003 | Davies et al. | |
| 6,681,003 B2 | 1/2004 | Linder et al. | |
| 6,697,671 B1 | 2/2004 | Nova et al. | |
| 6,801,137 B2 | 10/2004 | Eggers | |
| 6,820,057 B1 | 11/2004 | Loch et al. | |
| 6,826,425 B2 | 11/2004 | Bardy | |
| 6,829,501 B2 | 12/2004 | Nielsen et al. | |
| 6,847,892 B2 | 1/2005 | Zhou et al. | |
| 6,871,093 B2 | 3/2005 | Hansen | |
| 6,871,211 B2 | 3/2005 | Labounty et al. | |
| 6,885,894 B2 | 4/2005 | Stessman | |
| 6,897,788 B2 | 5/2005 | Khair et al. | |
| 6,898,462 B2 | 5/2005 | Rock et al. | |
| 6,907,283 B2 | 6/2005 | Carter et al. | |
| 6,937,150 B2 | 8/2005 | Medema et al. | |
| 6,940,403 B2 | 9/2005 | Kail, IV | |
| 6,944,498 B2 | 9/2005 | Owen et al. | |
| 6,955,864 B1 | 10/2005 | Vaisnys et al. | |
| 6,957,102 B2 | 10/2005 | Silver et al. | |
| 6,980,859 B2 | 12/2005 | Powers et al. | |
| 6,990,373 B2 | 1/2006 | Jayne et al. | |
| 7,006,865 B1 | 2/2006 | Cohen et al. | |
| 7,016,727 B2 | 3/2006 | Powers et al. | |
| 7,074,195 B2 | 7/2006 | Nelson et al. | |
| 7,085,601 B1 | 8/2006 | Bardy et al. | |
| 7,096,062 B2 | 8/2006 | Kelly et al. | |
| 7,107,096 B2 | 9/2006 | Fischell et al. | |
| 7,117,031 B2 | 10/2006 | Lohman et al. | |
| 7,120,488 B2 | 10/2006 | Nova et al. | |
| 7,129,836 B2 | 10/2006 | Lawson et al. | |
| 7,138,902 B2 | 11/2006 | Menard | |
| 7,162,306 B2 | 1/2007 | Caby et al. | |
| 7,231,258 B2 | 6/2007 | Moore et al. | |
| 7,238,156 B1 | 7/2007 | Adamczyk | |
| 7,245,964 B2 | 7/2007 | Moore et al. | |
| 7,257,440 B2 | 8/2007 | Morgan et al. | |
| 7,289,029 B2 | 10/2007 | Medema et al. | |
| 7,340,301 B2 | 3/2008 | Weiss et al. | |
| 7,343,197 B2 | 3/2008 | Shusterman | |
| 7,390,299 B2 | 6/2008 | Weiner et al. | |
| 7,439,705 B2 | 10/2008 | Koike | |
| 7,474,914 B2 | 1/2009 | Barr | |
| 7,477,933 B2 | 1/2009 | Ueyama | |
| 7,515,044 B2 | 4/2009 | Welch et al. | |
| 7,587,237 B2 | 9/2009 | Korzinov et al. | |
| 7,595,723 B2 | 9/2009 | Heitzmann et al. | |
| 7,653,435 B2 | 1/2010 | Halsne | |
| 7,715,913 B1 | 5/2010 | Froman et al. | |
| 7,761,261 B2 | 7/2010 | Shmueli et al. | |
| 7,782,192 B2 | 8/2010 | Jeckelmann et al. | |
| 7,953,478 B2 | 5/2011 | Vaisnys et al. | |
| 8,000,799 B2 | 8/2011 | Verhoef | |
| 8,005,552 B2 | 8/2011 | Covey et al. | |
| 8,086,320 B2 | 12/2011 | Saketkhou | |
| 8,090,441 B2 | 1/2012 | Chapman et al. | |
| 8,121,683 B2 | 2/2012 | Bucher et al. | |
| 8,147,486 B2 | 4/2012 | Honour et al. | |
| 8,183,823 B2 | 5/2012 | Neumiller et al. | |
| 8,260,413 B2 | 9/2012 | Heath | |
| 8,265,740 B2 | 9/2012 | Fischell et al. | |
| 8,265,907 B2 | 9/2012 | Nanikashvili et al. | |
| 8,271,082 B2 | 9/2012 | Donnelly et al. | |
| RE43,767 E | 10/2012 | Eggers et al. | |
| 8,277,377 B2 | 10/2012 | Quy | |
| 8,290,129 B2 | 10/2012 | Rogers et al. | |
| 8,290,574 B2 | 10/2012 | Feild et al. | |
| 8,301,245 B2 | 10/2012 | Garrett et al. | |
| 8,319,632 B1 | 11/2012 | Vaisnys et al. | |
| 8,331,574 B2 | 12/2012 | Powers | |
| 8,332,233 B2 | 12/2012 | Ott et al. | |
| 8,334,768 B2 | 12/2012 | Eaton et al. | |
| 8,335,562 B2 | 12/2012 | Hansen et al. | |
| 8,364,250 B2 | 1/2013 | Moon et al. | |
| 8,364,260 B2 | 1/2013 | Kumar | |
| 8,369,936 B2 | 2/2013 | Farringdon et al. | |
| 8,369,944 B2 | 2/2013 | Macho et al. | |
| 8,376,943 B2 | 2/2013 | Kovach et al. | |
| 8,419,644 B2 | 4/2013 | Eerden | |
| 8,425,414 B2 | 4/2013 | Eveland | |
| 8,425,415 B2 | 4/2013 | Tran | |
| 8,428,722 B2 | 4/2013 | Verhoef et al. | |
| 8,438,038 B2 | 5/2013 | Cosentino et al. | |
| 8,473,039 B2 | 6/2013 | Michelson et al. | |
| 8,477,026 B2 | 7/2013 | Bruegger et al. | |
| 8,480,577 B2 | 7/2013 | Tuccillo | |
| 8,498,701 B2 | 7/2013 | Vaisnys et al. | |
| 8,565,871 B2 | 10/2013 | Tuysserkani | |
| 8,587,427 B2 | 11/2013 | LaLonde et al. | |
| 8,600,491 B2 | 12/2013 | McMahon et al. | |
| 8,600,506 B2 | 12/2013 | Hahn et al. | |
| 8,608,654 B2 | 12/2013 | Carlberg et al. | |
| 8,620,418 B1 | 12/2013 | Kuppuraj et al. | |
| 8,639,346 B2 | 1/2014 | Seeberger et al. | |
| 8,666,488 B2 | 3/2014 | Duke | |
| 8,676,312 B2 | 3/2014 | Daynes et al. | |
| 8,702,603 B2 | 4/2014 | Bardy | |
| 8,706,225 B2 | 4/2014 | Matos | |
| 8,771,184 B2 | 7/2014 | Besson et al. | |
| 8,774,917 B2 | 7/2014 | Macho et al. | |
| 8,774,932 B2 | 7/2014 | Fahey | |
| 8,798,729 B2 | 8/2014 | Kaib et al. | |
| 2003/0158593 A1 | 2/2003 | Heilman | |
| 2003/0216786 A1 | 11/2003 | Russial | |
| 2004/0162586 A1 | 8/2004 | Covey et al. | |
| 2004/0171914 A1 | 9/2004 | Avni | |
| 2006/0136000 A1* | 6/2006 | Bowers | A61N 1/3925 607/5 |
| 2006/0149126 A1* | 7/2006 | Ertas | A61B 1/00059 600/101 |

(56) References Cited

U.S. PATENT DOCUMENTS

| | | | |
|---|---|---|---|
| 2006/0290496 A1* | 12/2006 | Peeters | A61B 5/0002 340/572.1 |
| 2007/0106145 A1 | 5/2007 | Kim et al. | |
| 2007/0115016 A1* | 5/2007 | Chang | G01R 31/2822 324/750.3 |
| 2008/0094228 A1 | 4/2008 | Welch et al. | |
| 2008/0281217 A1 | 11/2008 | Peterson et al. | |
| 2009/0028185 A1 | 1/2009 | Doerr et al. | |
| 2009/0152954 A1* | 6/2009 | Le | H02J 17/00 307/110 |
| 2009/0171227 A1 | 7/2009 | Dziubinski et al. | |
| 2009/0289776 A1* | 11/2009 | Moore | G06K 7/0008 340/10.41 |
| 2009/0299156 A1* | 12/2009 | Simpson | A61B 5/0002 600/301 |
| 2010/0057167 A1 | 3/2010 | Evers et al. | |
| 2010/0087883 A1 | 4/2010 | Sullivan et al. | |
| 2010/0174331 A1 | 7/2010 | Garrett et al. | |
| 2010/0198089 A1 | 8/2010 | Litovchick et al. | |
| 2010/0241181 A1 | 9/2010 | Savage et al. | |
| 2010/0249625 A1 | 9/2010 | Lin | |
| 2010/0249860 A1 | 9/2010 | Shuros et al. | |
| 2010/0268103 A1 | 10/2010 | McNamara et al. | |
| 2010/0331932 A1 | 12/2010 | Stevenson et al. | |
| 2011/0144707 A1 | 6/2011 | Sullivan et al. | |
| 2011/0166468 A1 | 7/2011 | Prystowsky et al. | |
| 2011/0213433 A1 | 9/2011 | Vaisnys et al. | |
| 2011/0213620 A1 | 9/2011 | Dziubinski | |
| 2011/0224747 A1 | 9/2011 | Maile et al. | |
| 2011/0288604 A1 | 11/2011 | Kaib et al. | |
| 2011/0288605 A1 | 11/2011 | Kaib et al. | |
| 2012/0011382 A1 | 1/2012 | Volpe et al. | |
| 2012/0071940 A1 | 3/2012 | Frank et al. | |
| 2012/0110226 A1 | 5/2012 | Vlach et al. | |
| 2012/0112903 A1 | 5/2012 | Kaib et al. | |
| 2012/0143025 A1 | 6/2012 | Porges et al. | |
| 2012/0146797 A1 | 6/2012 | Oskin et al. | |
| 2012/0158075 A1 | 6/2012 | Kaib et al. | |
| 2012/0190994 A1 | 7/2012 | Kim et al. | |
| 2012/0191147 A1 | 7/2012 | Rao et al. | |
| 2012/0197353 A1 | 8/2012 | Donnelly et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2013/0012827 A1 | 1/2013 | Kurzweil et al. | |
| 2013/0013014 A1 | 1/2013 | Donnelly et al. | |
| 2013/0046162 A1 | 2/2013 | Baumann et al. | |
| 2013/0060098 A1 | 3/2013 | Thomsen et al. | |
| 2013/0085364 A1 | 4/2013 | Lu et al. | |
| 2013/0085538 A1 | 4/2013 | Volpe et al. | |
| 2013/0144536 A1 | 6/2013 | Baker et al. | |
| 2013/0150698 A1 | 6/2013 | Hsu et al. | |
| 2013/0218252 A1 | 8/2013 | Kaib et al. | |
| 2013/0231711 A1 | 9/2013 | Kaib | |
| 2013/0261479 A1 | 10/2013 | Kemppainen et al. | |
| 2013/0304143 A1* | 11/2013 | Banville | A61N 1/39 607/5 |
| 2013/0317377 A1 | 11/2013 | Gupta et al. | |
| 2013/0324868 A1 | 12/2013 | Kaib et al. | |
| 2013/0325078 A1 | 12/2013 | Whiting et al. | |
| 2013/0331663 A1 | 12/2013 | Albert et al. | |
| 2014/0005506 A1* | 1/2014 | Elghazzawi | A61B 5/0205 600/324 |
| 2014/0018637 A1 | 1/2014 | Bennett et al. | |
| 2014/0025131 A1 | 1/2014 | Sullivan et al. | |
| 2014/0039593 A1 | 2/2014 | Savage et al. | |
| 2014/0046391 A1 | 2/2014 | Cowan et al. | |
| 2014/0070957 A1 | 3/2014 | Longinotti-Buitoni et al. | |
| 2014/0085081 A1 | 3/2014 | Brown et al. | |
| 2014/0085082 A1 | 3/2014 | Lyon et al. | |
| 2014/0088660 A1 | 3/2014 | Debardi et al. | |
| 2014/0107718 A1 | 4/2014 | Foote et al. | |
| 2014/0148869 A1 | 5/2014 | Stickney et al. | |
| 2014/0163334 A1 | 6/2014 | Volpe et al. | |
| 2014/0249613 A1 | 9/2014 | Kaib | |
| 2014/0296931 A1* | 10/2014 | Chapman | A61N 1/3918 607/7 |

* cited by examiner

SYSTEMS AND METHODS FOR UTILIZING IDENTIFICATION DEVICES IN A WEARABLE MEDICAL THERAPY DEVICE

CROSS REFERENCE TO RELATED APPLICATIONS

This application claims the benefit of U.S. Provisional Patent Application Ser. No. 61/861,110 entitled "Compact Controller Device for Defibrillator" filed Aug. 1, 2013, U.S. Provisional Patent Application Ser. No. 62/021,609 entitled "Wearable Defibrillator" filed Jul. 7, 2014, and U.S. Provisional Patent Application Ser. No. 62/025,660 entitled "Wearable Defibrillator" filed Jul. 17, 2014, all of which are incorporated herein by reference.

BACKGROUND OF THE INVENTION

Field of the Invention

The present disclosure generally relates to the treatment of heart defects by the administration of electrical therapy and, more particularly, to a defibrillator for imparting the electrical therapy to the heart.

Description of Related Art

Technology is available for correcting excessively slow heart rates (bradycardia) using implantable devices, commonly referred to as pacemakers, which deliver microjoule electrical pulses to a slowly beating heart in order to speed the heart rate up to an acceptable level. Also, it is well known to deliver high energy shocks (e.g., 180 to 360 joules) via external paddles applied to the chest wall in order to correct excessively fast heart rates, and prevent the possible fatal outcome of ventricular fibrillation or certain ventricular tachycardias. Bradycardia, ventricular fibrillation, and ventricular tachycardia are all electrical malfunctions (arrhythmias) of the heart. Each may lead to death within minutes unless corrected by the appropriate electrical stimulation.

One of the most deadly forms of heart arrythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death may result in minutes if normal heart contractions are not restored. Although frequently not noticeable to the victim, ventricular fibrillation is often preceded by ventricular tachycardia, which is a regular but fast rhythm of the heart. Because the victim has no noticeable warning of the impending fibrillation, death often occurs before the necessary medical assistance can arrive.

Because time delays in applying the corrective electrical treatment may result in death, implantable pacemakers and defibrillators have significantly improved the ability to treat these otherwise life-threatening conditions. Being implanted within the patient, the device continuously monitors the patient's heart for treatable arrhythmias and, when such is detected, the device applies corrective electrical pulses directly to the heart.

Normal heart function often can be restored to a person suffering ventricular fibrillation or ventricular tachycardia by a procedure known as cardioversion, the synchronized application of electrical therapy to the heart muscle. Pacemakers and defibrillators that apply corrective electrical pulses externally to the patient's chest wall also are used to correct such life-threatening arrhythmias, but suffer from a drawback insofar as it may not be possible to apply the device in time during an acute arrhythmic emergency to save the patient's life. Such treatment is needed within a few minutes to be effective.

Consequently, when a patient is deemed at high risk of death from such arrhythmias, electrical devices often are implanted so as to be readily available when treatment is needed. However, patients that have recently had a heart attack or are awaiting such an implantable device, may be kept in a hospital where corrective electrical therapy is generally close at hand. Long-term hospitalization is frequently impractical due to its high cost, or due to the need for patients to engage in normal daily activities.

Defibrillators have been developed for patients that have recently experienced a heart attack, that are susceptible to heart arrhythmias and are at temporary risk of sudden death, and that are awaiting an implantable device. However, current wearable defibrillators may lack the required size and durability to provide maximum comfort and usability to the patient.

Accordingly, a need exists for a portable, wearable defibrillator that is small, lightweight, and extremely durable.

SUMMARY OF THE INVENTION

According to one aspect of the invention, a system is provided that comprises: at least one identification device associated with a wearable medical therapy device and configured to have information read therefrom and written thereto; at least one controller operatively connected to the at least one identification device and configured to at least one of retrieve the information from the at least one identification device and write the information to the at least one identification device; and at least one device positioned externally from the wearable medical therapy device and configured to interrogate the at least one identification device to at least one of obtain the information from the at least one identification device and write additional information to the at least one identification device.

The at least one identification device may be a radio frequency identification (RFID) module comprising at least an RFID transceiver and antenna. The antenna may be spaced from a backup battery within a housing of the wearable medical device. The wearable medical therapy device may be a wearable defibrillator. The at least one identification device may have information identifying the wearable medical therapy device stored thereon that can be accessed by the at least one device positioned externally from the wearable medical therapy device such that the wearable medical therapy device can be identified thereby.

The at least one controller may be configured to write problems that occur with the wearable medical therapy device during patient field use to the at least one identification device, and the at least one identification device may be interrogated by the at least one device positioned externally from the wearable medical therapy device to obtain the problems that have been written to the at least one identification device such that the problems can be diagnosed by service personnel.

The additional information that is written to the at least one identification device may comprise shipping information, such as, but not limited to, shipping boxes, software versions, board revisions, and assembly revisions.

The information written to the at least one identification device by the at least one controller may comprise patient parameters of a patient utilizing the wearable medical therapy device. The at least one device positioned externally from the wearable medical therapy device may be configured to interrogate the at least one identification device to obtain the patient parameters therefrom. The at least one device positioned externally from the wearable medical therapy device may be configured to communicate with at least one second identification device associated with a second wearable medical therapy device to write the patient parameters to the at least one second identification device. At least one controller of the second wearable medical therapy device may be configured to read the patient parameters from the at least one second identification device and store the patient parameters.

The additional information written to the at least one identification device by the at least one device positioned externally from the wearable medical therapy device may be a command to at least one of enter into a test mode and initiate a self-test. The at least one controller may be configured to read the command from the at least one identification device and at least one of enter into the test mode and begin the self-test.

The at least one identification device may be a storage device having reading and writing capabilities and wireless communication capabilities or wired communication capabilities. Examples of storage devices having wireless communication capabilities include, but are not limited to, a cellular-ready storage device, a Wi-Fi-ready storage device, and a short-range wireless communication protocol-ready storage device. Examples of storage devices having wired communication capabilities include, but are not limited to, a flash drive, a USB device, a mini-USB device, a SD card, a miniSD card, and a microSD card.

According to another aspect of the invention, provided is a method for utilizing at least one identification configured to have information read therefrom and written thereto associated with a wearable medical therapy device. The method comprises: at least one of retrieving the information from the at least one identification device and writing the information to the identification device by at least one controller operatively connected to the at least one identification device; and interrogating the at least one identification device by at least one device positioned externally from the wearable medical therapy device to at least one of obtain the information from the at least one identification device and write additional information to the at least one identification device.

According to yet another aspect of the invention, provided is a method for servicing a wearable medical therapy device. The method comprises: configuring at least one identification device associated with the wearable medical therapy device to have problems that occur with the wearable medical therapy device during patient field use written thereto by at least one controller operatively connected to the at least one identification device; and interrogating the at least one identification device by at least one device positioned externally from the wearable medical therapy device to obtain the written problems for diagnosis of the problems by service personnel.

According to still another aspect of the invention, provided is a method for cloning patient parameters from a first wearable medical therapy device to a second wearable medical therapy device. The method comprises: configuring at least one first identification device associated with the first wearable medical therapy device to have patient parameters of a patient utilizing the first wearable medical therapy device written thereto by at least one first controller operatively connected to the at least one first identification device; interrogating the at least one first identification device by at least one device positioned externally from the first wearable medical therapy device to obtain the written patient parameters; establishing communication between the at least one device positioned externally from the first wearable medical therapy device and at least one second identification device associated with the second wearable medical therapy device; rewriting the written patient parameters to the at least one second identification device; reading the rewritten patient parameters by at least one second controller operatively connected to the at least one second identification device; and storing the read patient parameters in a memory operatively connected to the at least one second controller.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE INVENTION

As used herein, spatial or directional terms, such as "inner", "left", "right", "up", "down", "horizontal", "vertical" and the like, relate to the invention as it is described herein. However, it is to be understood that the invention can assume various alternative orientations and, accordingly, such terms are not to be considered as limiting. For the purposes of this specification, unless otherwise indicated, all numbers expressing quantities of ingredients, reaction conditions, dimensions, physical characteristics, and so forth used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

Figure 1:
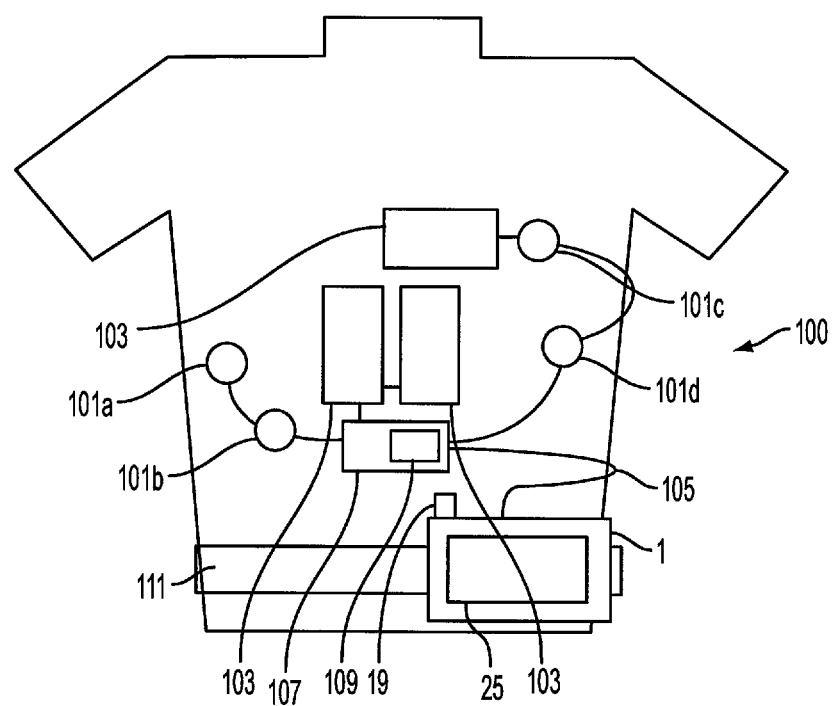
FIG. 1 is a schematic view of a wearable defibrillator in accordance with the invention.

With reference to FIG. 1, a medical therapy device may be configured as a wearable defibrillator, denoted generally as reference numeral 100, such as the LifeVest® wearable defibrillator available from ZOLL® Lifecor Corporation of Pittsburgh, Pa. The wearable defibrillator 100 may be worn by a patient and may include a belt or harness or other apparel configured to permit the patient to wear the defibrillator 100. Such wearable defibrillators may be typically worn nearly continuously for two to three months at a time. During the period of time in which they are worn by the patient, the wearable defibrillator 100 may be configured to continuously monitor the vital signs of the patient, to be user-friendly and accessible, to be as light-weight, comfortable, and portable as possible, and to be capable of delivering one or more life-saving therapeutic shocks when needed.

The wearable defibrillator 100 may comprise a monitor unit 1 positioned within an external housing 3 that is configured to be worn by a patient and connected to a therapeutic or treatment device, such as an upper body harness or vest that includes ECG electrodes 101a, 101b, 101c, and 101d and therapy pads 103. The ECG electrodes 101a, 101b, 101c, and 101d and therapy pads 103 of the harness or vest are operatively connected to the monitor unit 1 via a trunk cable 105 or other suitable connection mechanism. Non-limiting examples of suitable wearable defibrillators are disclosed in U.S. Pat. Nos. 4,928,690; 5,078,134; 5,741,306; 5,944,669; 6,065,154; 6,253,099; 6,280,461; 6,681,003; 8,271,082; and 8,369,944; the entirety of all of which are incorporated by reference herein. The upper body harness or vest may also include other sensing electrodes (not shown) such as heart beat sensors, accelerometers, and sensors capable of measuring blood pressure, heart rate, thoracic impedance, respiration rate, heart sounds, acoustic sensors, audio transducers, and the activity level of the subject.

Electrodes 101a, 101b, 101c, and 101d are removably attached to the patient when the wearable defibrillator 100 is worn by the patient. The electrodes 101a, 101b, 101c, and 101d form part of an electrode assembly 107. According to one example, the electrode assembly 107 receives ECG signals from a front-to-back channel and from a side-to-side channel. The front-to-back (FB) channel includes an electrode 101a, 101b, 101c, and 101d positioned on the chest of the patient and another electrode 101a, 101b, 101c, and 101d positioned on the back of the patient. The side-to-side (SS) channel includes an electrode 101a, 101b, 101c, and 101d positioned on the left side of the chest and another electrode 101a, 101b, 101c, and 101d positioned on the right side of the patient.

The monitor unit 1 is operatively connected to the therapy pads 103, at least one tactile stimulator 109, and electrode assembly 107. The therapy pads 103 are removably connected to the patient when the defibrillator 100 is worn. Optionally, the monitor unit 1 may be operatively connected to other electrodes/devices which provide data to the controller regarding other physiological conditions or parameters of the patient.

While a trunk cable 105 may be used to connect the electrode assembly 107 to the monitor unit 1, other types of cables or other connection devices to operatively connect the electrode assembly 107 to the monitor unit 1 may also be used. Wiring or other connection devices may be used to connect at least one portion of the electrode assembly 107 to the electrodes 101a, 101b, 101c, and 101d. In addition, the monitor unit 1 may alternatively be operatively connected to one or more of the electrodes 101a, 101b, 101c, and 101d, therapy pads 103, electrode assembly 107, and tactile stimulator 109 by a wireless connection or a combination of wireless and wired connections.

In some embodiments, the monitor unit 1 may include, without limitation, one or more processors, one or more controllers, and/or one or more programs or other software stored in memory operatively connected to one or more processors, as will be discussed in greater detail hereinafter.

Figure 2:
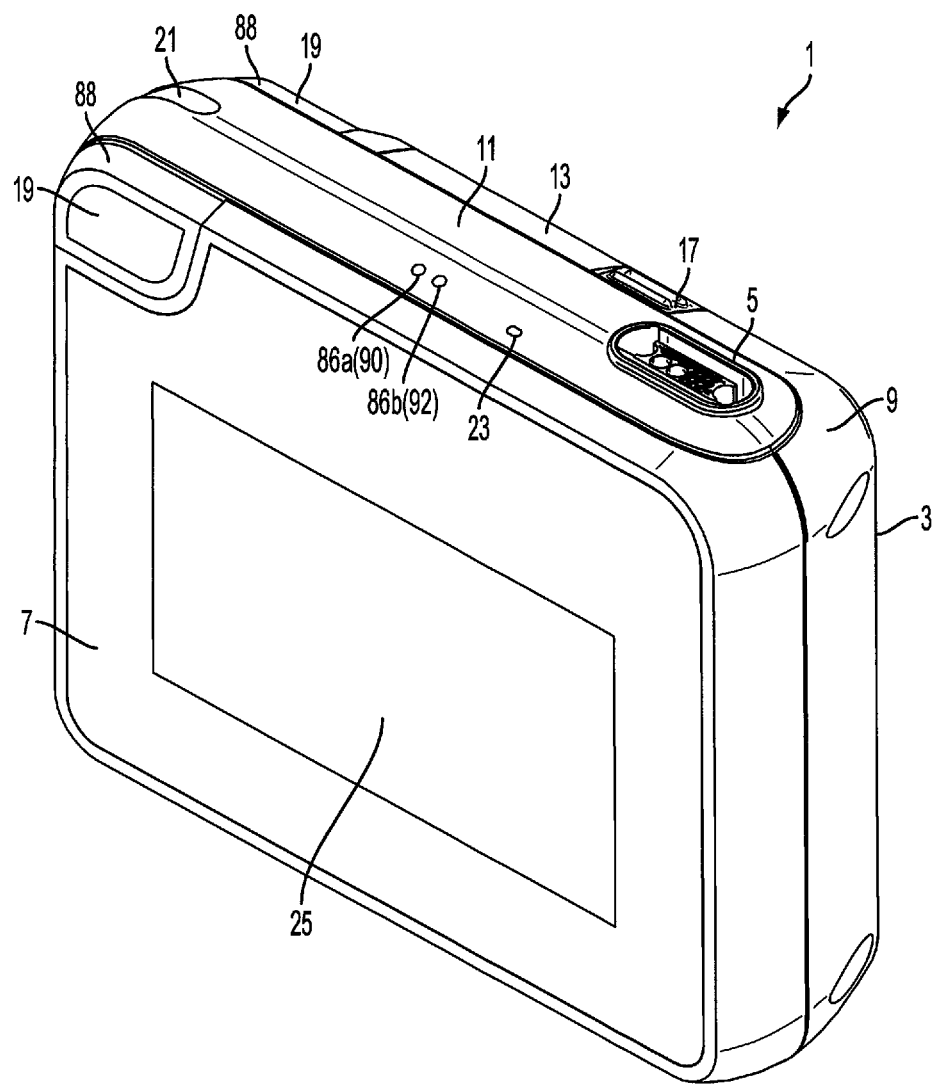
FIG. 2 is a front perspective view of the external housing of a monitor unit of a defibrillator in accordance with the invention.
Figure 3:
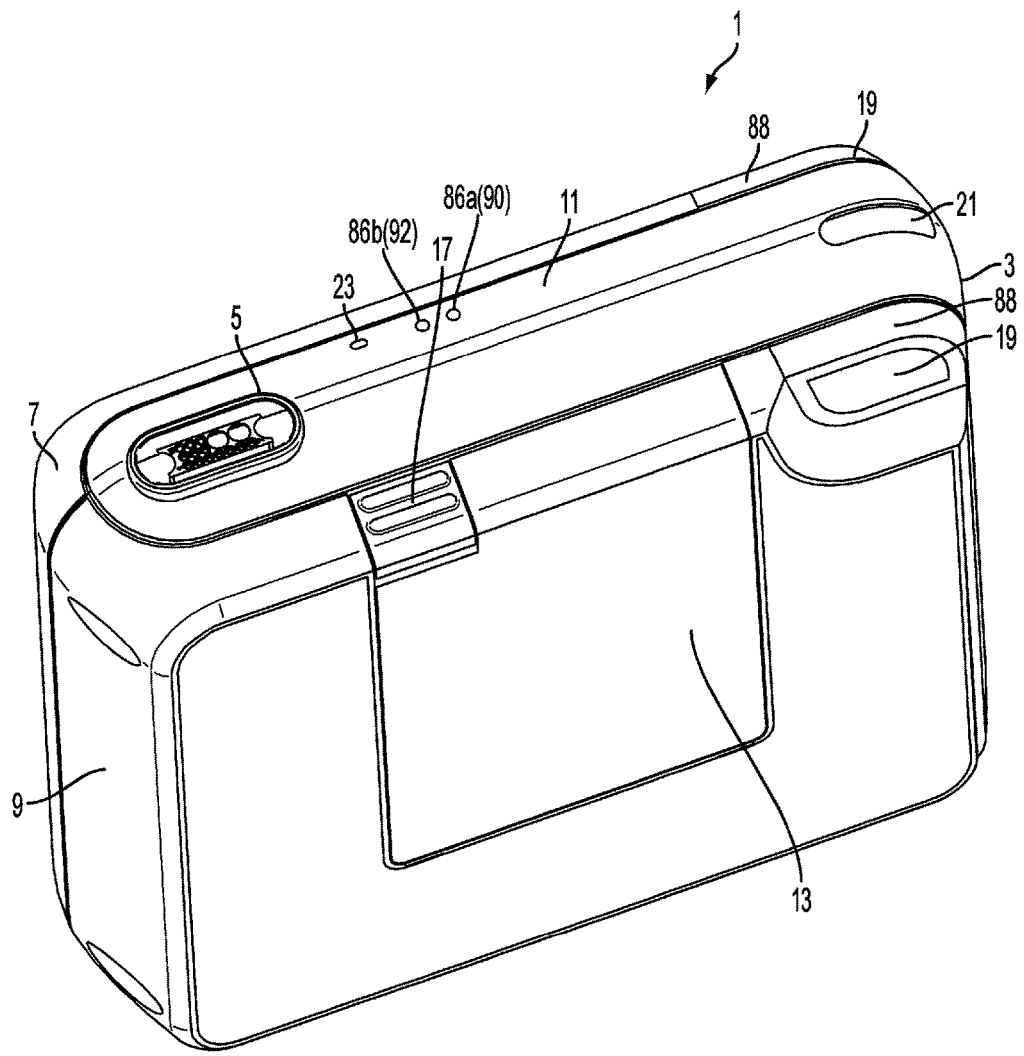
FIG. 3 is a rear perspective view of the external housing of FIG. 2.
Figure 4:
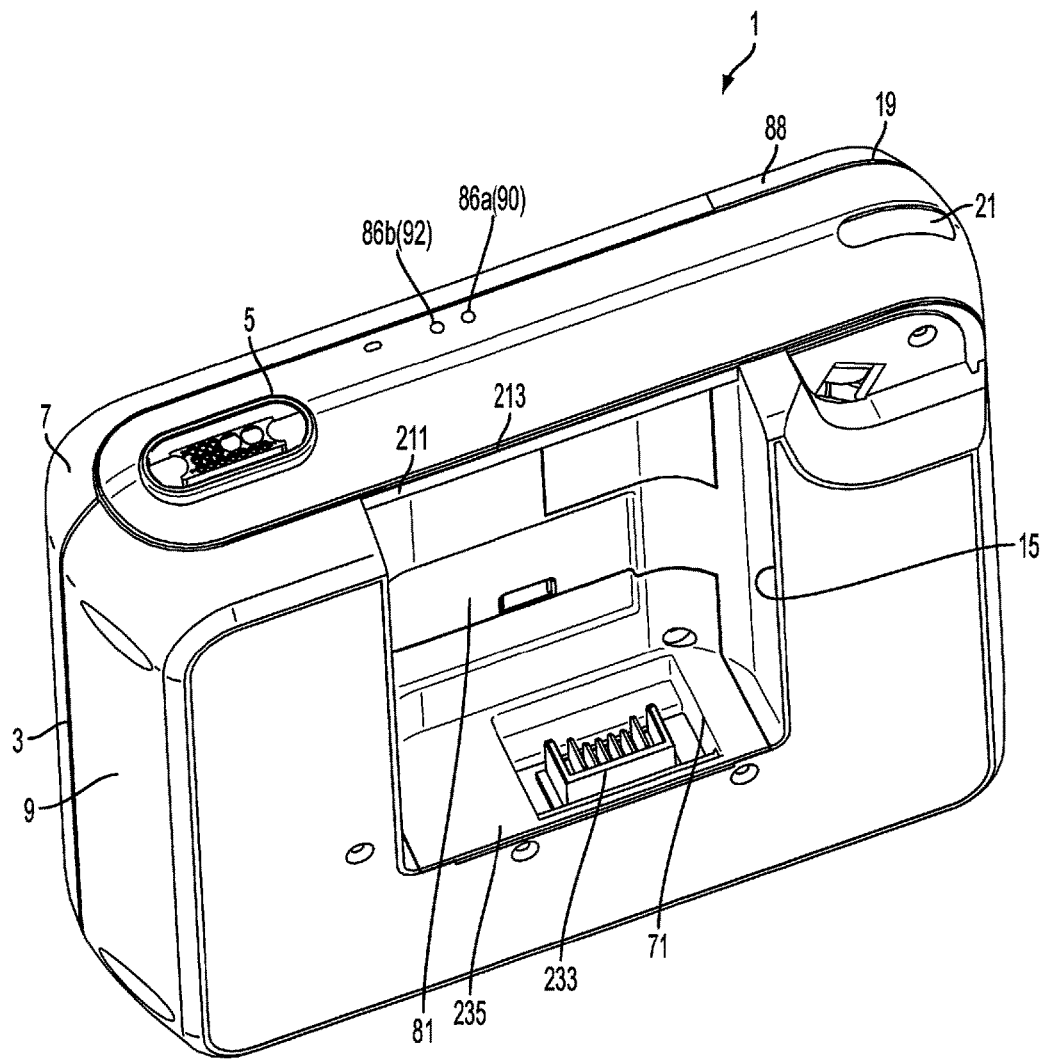
FIG. 4 is a rear perspective view of the external housing of FIG. 2 with a top cover plate and battery pack removed.

With reference to FIGS. 2-4, the monitor unit 1 is configured to implement the functions of monitoring an ambulatory patient's ECG information and, when needed, administering a therapeutic shock to the patient. The monitor unit 1 comprises a distributed printed circuit board 41 positioned within an external housing 3 configured to be worn by a patient and connected to a therapeutic or treatment device, such as an upper body harness or vest that includes ECG electrodes 101a, 101b, 101c, and 101d and therapy pads 107 as discussed hereinabove. The ECG electrodes 101a, 101b, 101c, and 101d and therapy pads 107 of the harness or vest are operatively coupled to the distributed printed circuit board 41 within the external housing 3 via a port 5. Such wearable therapeutic devices are described in U.S. Pat. No. 5,741,306 and United States Patent Publication No. 2012/0011382, which are assigned to the assignee of the present application and are hereby incorporated by reference in their entirety.

In some embodiments, the external housing 3 of the monitor unit 1 comprises a front cover 7, a rear cover 9, and a top cover 11. A rechargeable and removable battery pack 13 is positioned within a battery well 15 provided in the rear cover 9. The battery pack 13 is secured to the rear cover 9 by a battery latching mechanism 17. The battery latching mechanism 17 is positioned at the top left corner of the battery pack 13 to allow for the battery pack 13 to be removed from the external housing 3 with one rocking motion. This rocking motion increases usability for patients with decreased dexterity, such as a patient with arthritis. The battery pack 13 has sufficient capacity to administer one or more therapeutic shocks to the therapeutic electrodes as well as provide power to all of the internal components of the defibrillator 1.

With reference to FIGS. 6-9, the battery pack 13 is designed to: a) allow for placing and replacing the battery to avoid fine motor control or simultaneous actions; b) allow for placing and replacing the battery to accommodate patients with limited reach and strength; c) provide the battery with a surface/texture that makes it easy to grip and control; d) provide insertion and removal of the battery to avoid simultaneous actions such as depressing and pulling; and e) provide battery insertion to allow for positive feedback, such as an audible indication that the battery is properly inserted.

The battery pack 13 may include a body 201 having a front side 203, rear side 205, top side 207, and bottom side 209. Desirably, the body 201 of the battery pack 13 has a substantially parallelepiped shape and is manufactured from plastic or any other suitable material. The latching mechanism 17 may be positioned at one of the upper corners of the top side 207 of the body 201 and is configured to be placed in an extended position to grasp a portion 211 (see FIG. 3) of an upper edge 213 of the battery well 15 when the battery pack 13 is positioned within the battery well 15 and a depressed position to allow removal of the battery pack 13 from the battery well 15.

Figure 10:
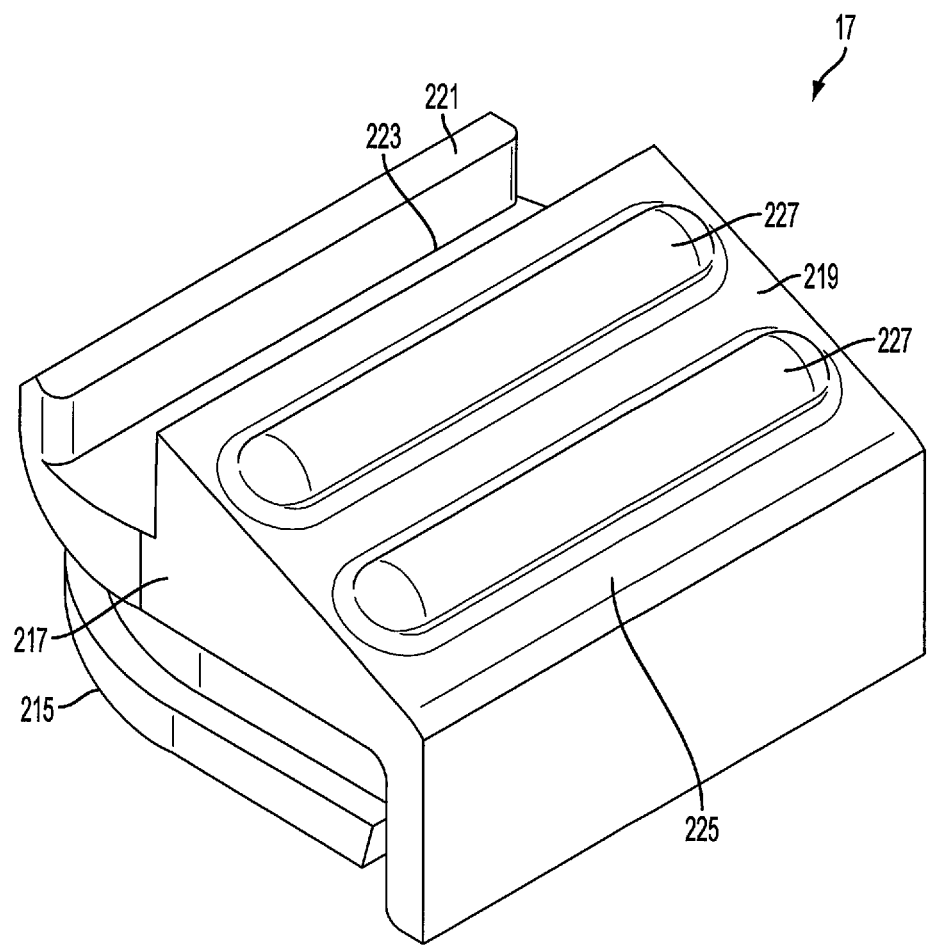
FIG. 10 is a front perspective view of a latching mechanism for use with the battery pack of FIG. 6.
Figure 11:
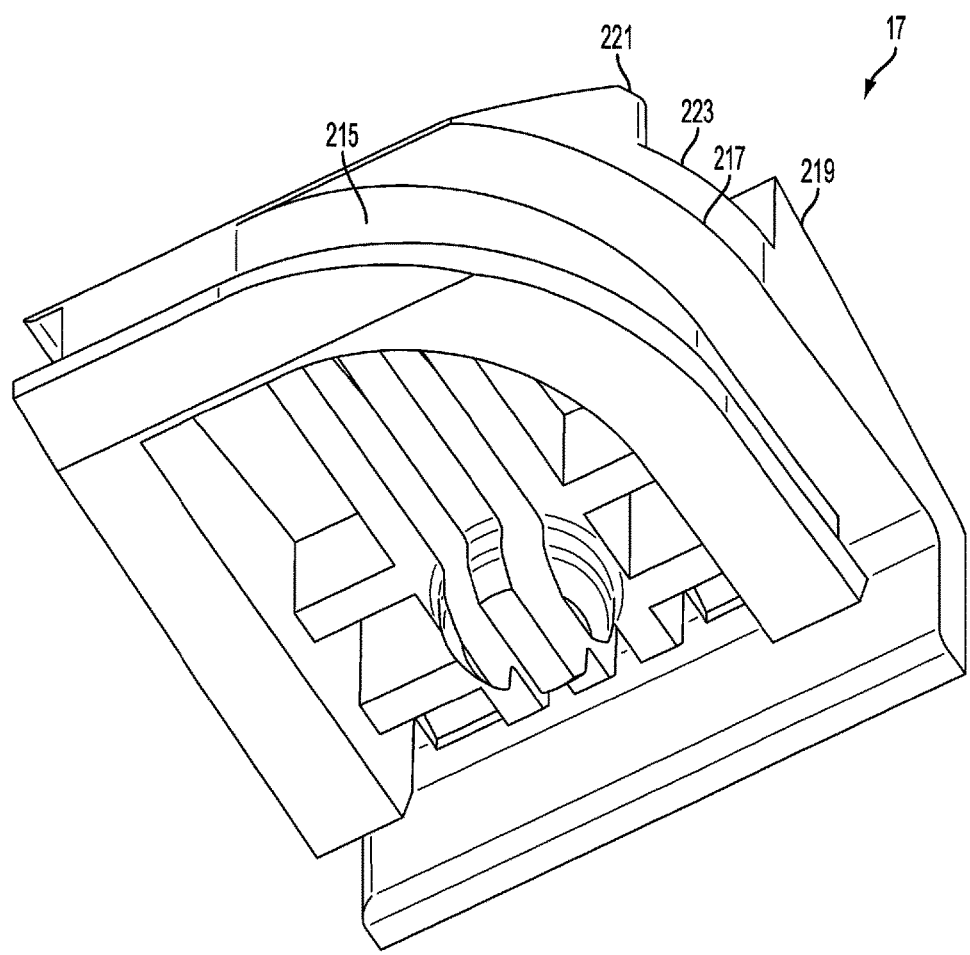
FIG. 11 is a bottom perspective view of the latching mechanism of FIG. 10.
Figure 12:
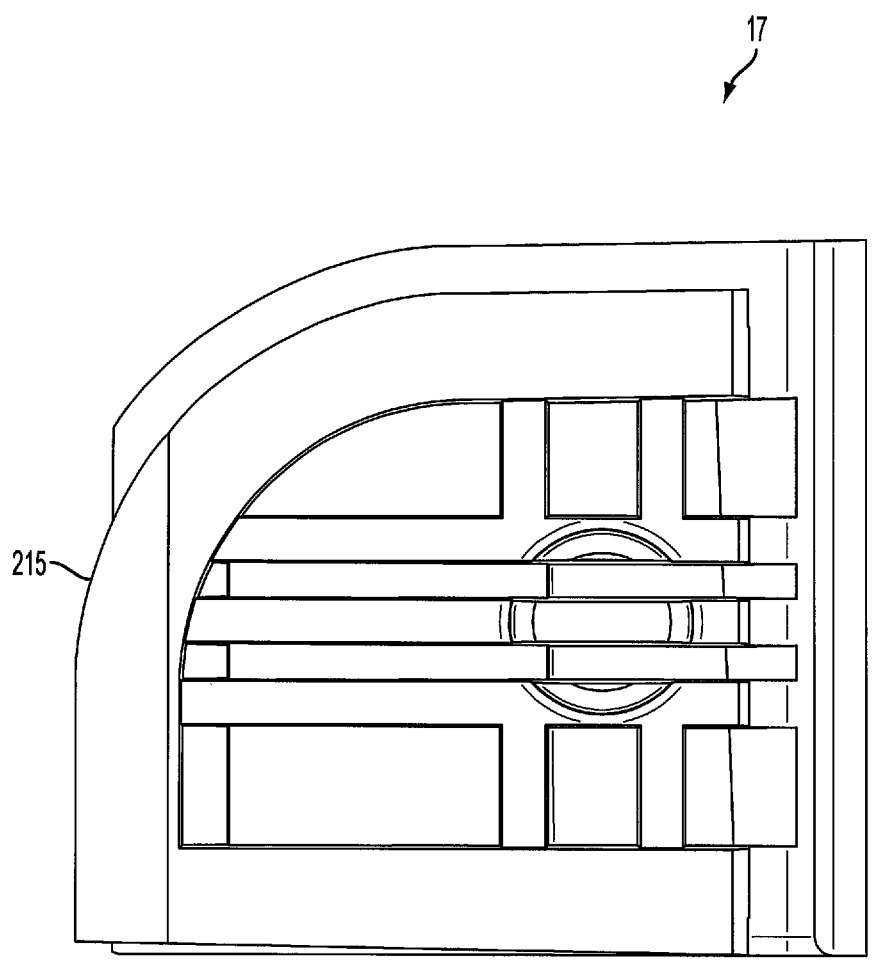
FIG. 12 is a bottom view of the latching mechanism of FIG. 10.

The latching mechanism 17 of the battery pack 13 desirably comprises a single latch that is automatically engaged when the battery is slid into position, and deactivated with a downward pushing action of a single finger. With specific reference to FIGS. 10-12, the latching mechanism 17 may comprise a body 215 having a top surface 217 with a finger engaging portion 219 and a flange member 221 extending therefrom and a channel 223 positioned between the flange member 221 and the finger engaging portion 219. The portion 211 of the upper edge 213 of the battery well 15 is grasped in the channel 223 when the latching mechanism 17 is in the extended position. The finger engaging portion 219 may have a downwardly angled front face 225 with at least one ridge 227 provided thereon. Desirably, two ridges 227 are provided that are manufactured from a rubber or other suitable material.

The battery pack 13 also includes a biasing element 229 (see FIG. 5) positioned within the body 215 of the latching mechanism 17. The biasing element 229 is configured to bias the latching mechanism 17 to the extended position. The battery pack 13 further includes a contact mechanism 231 extending from the bottom side 209 of the body 201 of the battery pack 13. The contact mechanism 231 may be configured to engage a corresponding contact mechanism 233 of the battery well 15 of the monitor unit 1. The contact mechanism 231 may be positioned asymmetrically relative to a longitudinal axis Y of the body 201 of the battery pack 13 to prevent the battery pack 13 from being inserted incorrectly into the battery well 15 and so that the correct orientation to insert the battery pack 13 into the battery well 15 is apparent to the user. The battery pack 13 may also include an extension member 232 (see FIG. 9) that is configured to cover an access opening 81 for an SD card or other memory device, as will be discussed hereinafter when the battery pack 13 is positioned within the battery well 15.

The battery pack 13 houses rechargeable cells. Two battery packs 13 may be supplied to a patient to provide continuous device use while one is charging. When fully charged, the battery pack 13 may provide power to monitor the patient for a minimum of 24 hours at an ambient temperature of 20° C. (with the patient wearing the device), with sufficient reserve capacity to deliver at least one 5-pulse defibrillating sequence at the maximum joule setting (150 joules) (−5%/+5% into a 50 ohm resistive load). The battery pack 13 also provides sufficient capacity to support full energy pacing for 60 minutes at the end of a 24 hour monitoring period.

Figure 5:
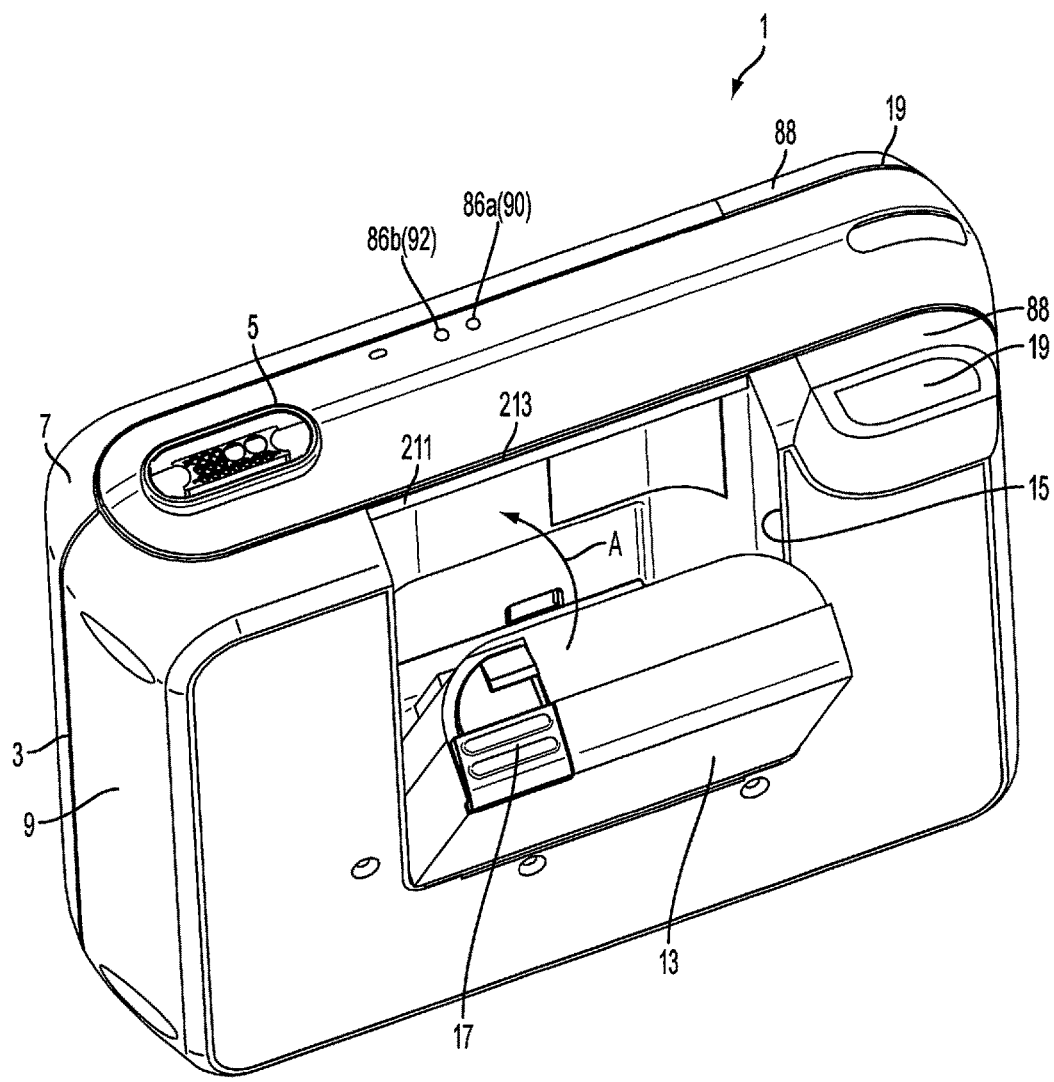
FIG. 5 is a rear perspective view of the external housing of FIG. 2 with the battery pack partially inserted.
Figure 6:
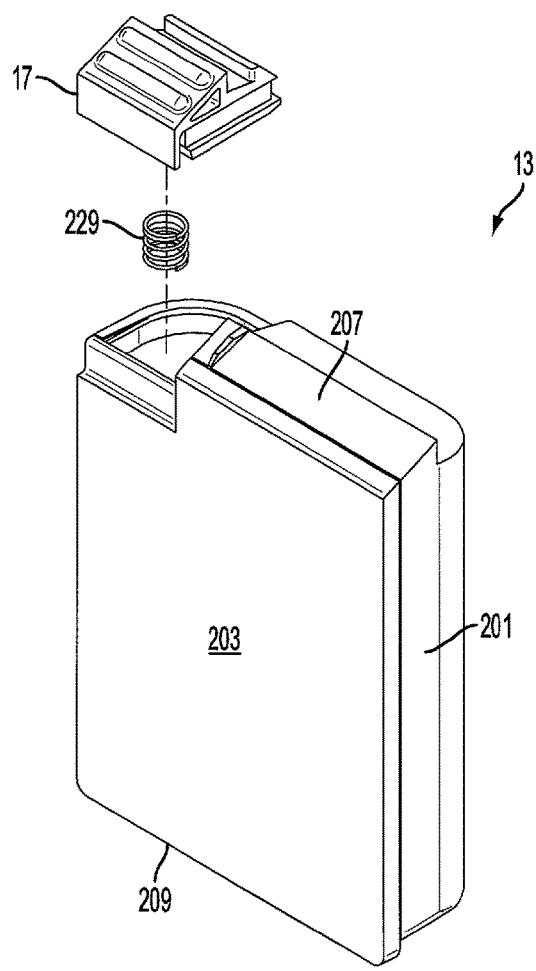
FIG. 6 is an exploded perspective view of a battery pack for use with a defibrillator.
Figure 7:
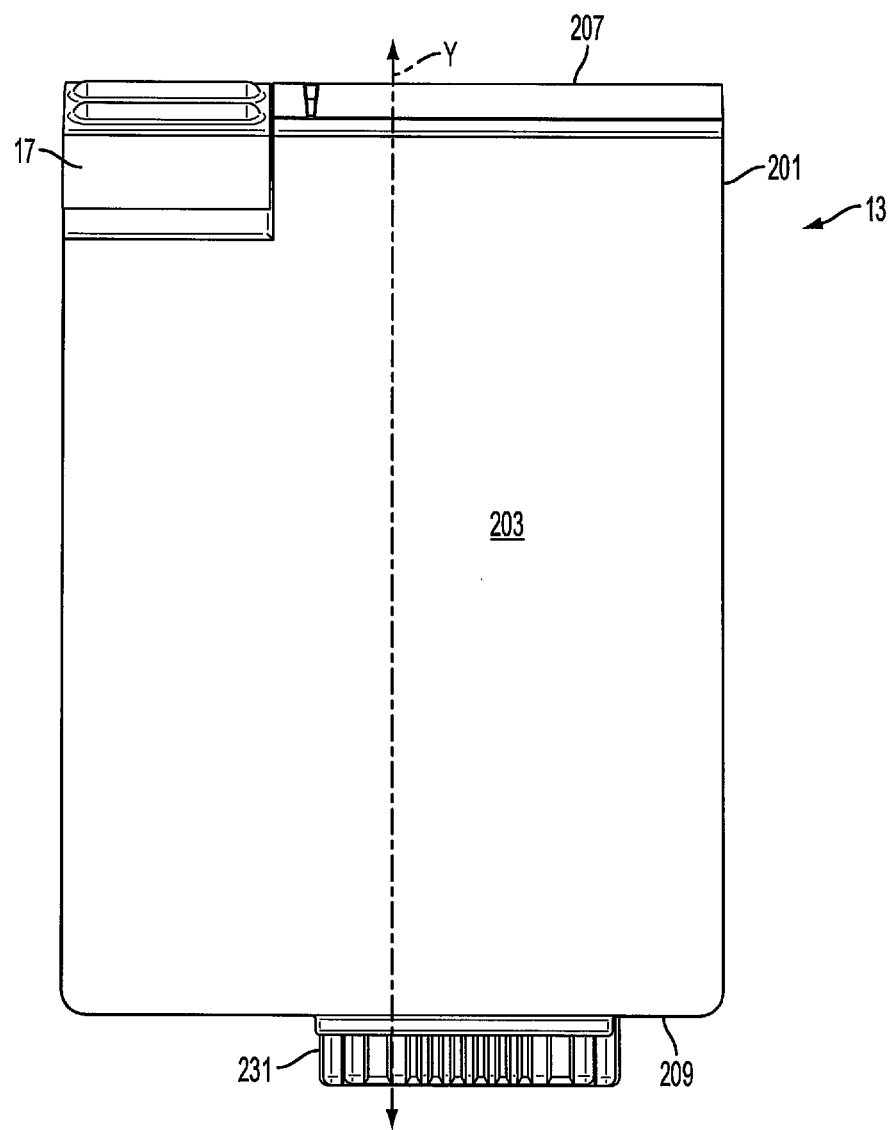
FIG. 7 is an assembled front view of the battery pack of FIG. 6.
Figure 8:
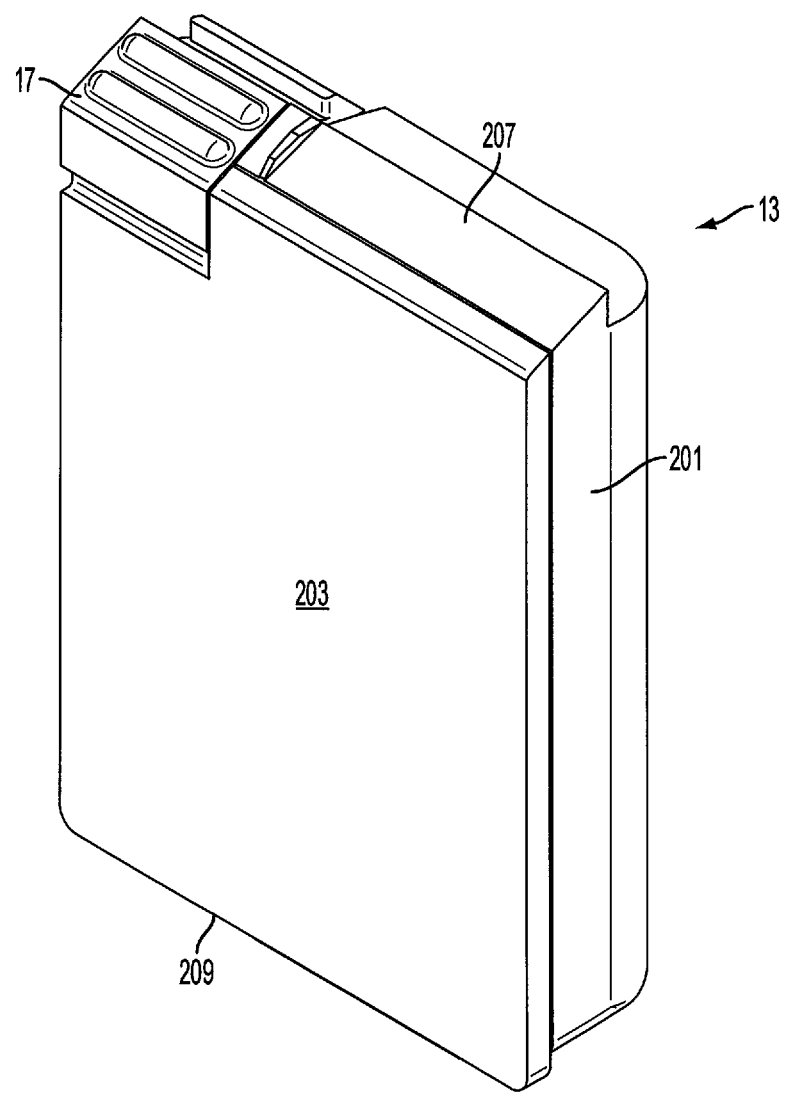
FIG. 8 is an assembled perspective view of the battery pack of FIG. 6.
Figure 9:
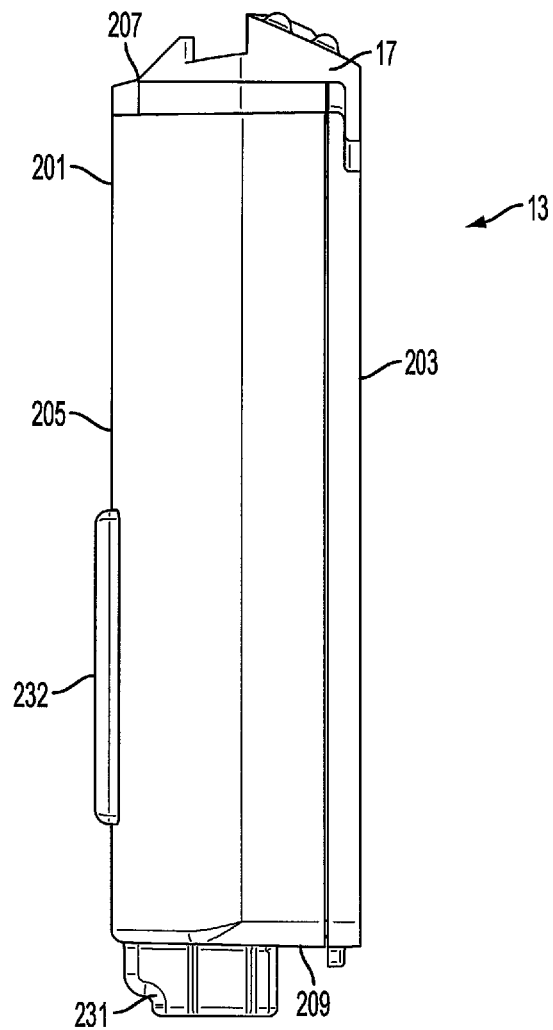
FIG. 9 is an assembled side view of the battery pack of FIG. 6.

With specific reference to FIG. 5, in operation, the battery pack 13 is inserted into the battery well 15 by orienting the bottom side 209 of the body 201 with a bottom edge 235 of the battery well 15 and rotating the battery pack 13 in the direction of arrow A into the battery well 15 such that the latching mechanism 17 engages the portion 211 of the upper edge 213 of the battery well 15 to move the latching mechanism 17 to the depressed position and continued rotation of the battery pack 13 allows the latching mechanism 17 to return to the extended position to grasp the portion 211 of the upper edge 213 of the battery well 15 within the channel 223 of the latching mechanism 17. The latching mechanism 17 is configured to provide an audible indication, such as a "snap" or "click", when it returns to the extended position and grasps the portion 211 of the upper edge 213 of the battery well 15 to provide feedback to the user that the battery pack 13 is properly installed.

The battery pack 13 may be removed from the battery well 15 by pressing on the latching mechanism 17 to move the latching mechanism 17 into the depressed position, thereby disengaging the portion 211 of the upper edge 213 of the battery well 15 from the channel 223 of the latching mechanism 17, and rotating the battery pack 13 away from the battery well 15. Accordingly, removal of the battery pack 13 can be accomplished with one hand.

As mentioned hereinabove, the external housing 3 of the monitor unit 1 is configured to be worn by the patient and is, accordingly, sized such that it does not interfere with the patient's movement and activity. More particularly, the external housing 3 may have a length of about 5 to 6 inches, a height of about 4 to 5 inches, and a width of about 1 to 2 inches. Desirably, the weight of the monitor unit 1 is 1.8 pounds.

Returning to FIGS. 2-4, in some embodiments, the external housing 3 further comprises a pair of patient response buttons 19 positioned, for example, in the top left corner of the housing 3. The response buttons 19 are positioned a small distance apart, desirably less than 1.5 inches. The location of the response buttons 19, and the distance between the response buttons 19, was chosen to enable patients with limited dexterity to easily and quickly operate the response buttons 19. The response buttons 19 may further incorporate a light emitting diode (LED) therein so that they can be illuminated to provide a visual indication to a patient as discussed in greater detail hereinafter.

In some embodiments, the monitor unit 1 further comprises an audio system having a speaker port 21 and a microphone port 23 positioned on the external housing 3. The speaker port 21 is desirably positioned at least 2.5 inches away from the microphone port 23 to minimize feedback. In addition, the speaker port 21 and the microphone port 23 can be located on the top cover 11 of the external housing 3 in order to face the patient for better orientation and functionality. The speaker port 21 is also positioned on an upper corner of the external housing 3 and wraps from the top of the external housing 3 to a side thereof. This allows the speaker port 21 to be more difficult to block if the top of the monitor unit 1 is obstructed. In addition, the speaker is mounted in a reverberator which uses a specific volume of air to artificially amplify audio at specific frequencies. The outlet of the reverberator is the speaker port 21. In one non-limiting embodiment, the reverberator is tuned to amplify the alarm frequencies at 2.272 kHz and 2.5 kHz in order to get to 95 dB at 1 m for the alarm. The microphone port 23 and the speaker port 21 are covered by a mesh or other suitable covering to prevent the ingress of fluid and/or particles into the external housing 3.

The external housing 3 of the monitor unit 1 also includes a display screen 25 for providing information to a patient and for providing a user input device to the patient. The display screen 25 provides information such as, but not limited to, time, battery life, volume, signal strength, device status, and any other useful information to the patient. In addition, the display screen 25 also allows the user to access various data regarding the monitor unit 1 such as, but not limited to, the settings of the device, data stored by the device, and various other data accumulated by the monitor unit 1. The display screen 25 further acts as a communication interface to allow the patient to send and receive data.

The display screen 25 may be any suitable capacitive touch screen device. For instance, the display screen 25 may include a 1.1 mm thick Dragontrail™ lens, manufactured by Asahi Glass Co. of Tokyo, JP, which supports a projected capacitive touch screen having a 4.3 inch LCD on the reverse side. A glass display may be provided to cover the entire front of the monitor unit 1, except for the response buttons 19, to provide the monitor unit 1 with a smooth, finished look and feel.

In operation and, as will be discussed in greater detail hereinafter, if the monitor unit 1 detects an abnormal condition, the monitor unit 1 is configured to stimulate the patient for a predetermined time period. The stimulus may be any stimulus perceptible by the patient. Examples of stimuli that the monitor unit 1 may produce include visual (via the display screen 25 and/or indicator LEDs discussed in greater detail hereinafter), audio (via the speaker port 21), tactile stimulation (via tactile stimulator 109) or a mild stimulating alarm shock (via the therapy pads 103). The response buttons 19 are provided to allow a user to turn off the stimulus by pressing both of the response buttons 19 within the predetermined time period. By pressing both of the response buttons 19, the stimulus is ceased and no further action is taken by the monitor unit 1. If the patient does not press both of the response buttons 19 within the predetermined time period, the monitor unit 1 administers one or more therapeutic shocks to the therapy pads 103.

With reference to FIGS. 13-16, and with continuing reference to FIGS. 2-4, the functional components of the monitor unit 1 are illustrated. The functional components of the monitor unit 1 are provided on a distributed printed circuit board, denoted generally as reference numeral 41, such as a rigid flex printed circuit board. Rigid flex printed circuit boards are boards using a combination of flexible and rigid board technologies. The rigid flex board can comprise multiple layers of flexible circuit substrates embedded within one or more rigid boards. Rigid flex printed circuit boards are designed in a three-dimensional space, which offers greater spatial efficiency. In addition, through the use of rigid flex printed circuit boards, all board-to-board connections have been eliminated, thereby increasing the durability of the monitor unit 1.

The distributed printed circuit board 41 comprises a discharge module 43, an energy storage module 45, a controller module 47, and, optionally, a communication module 49. The discharge module 43 is disposed on a first portion 51 of the distributed printed circuit board 41 and is for selectively delivering an energy pulse to the patient. The energy storage module 45 is disposed on a second portion 53 of the distributed printed circuit board 41. The energy storage module 45 is operatively connected to the discharge module 43 by a first flexible member 55. The controller module 47 is provided to control the delivery of the energy pulse to the patient and is disposed on a third portion 57 of the distributed printed circuit board 41. The controller module 47 is operatively connected to the energy storage module 45 by a second flexible member 59. The communication module 49 can be disposed on a fourth portion 61 of the distributed printed circuit board 41 and can be operatively connected to the controller module 47 by a third flexible member 63.

The discharge module 43 and the energy storage module 45 can be considered high-voltage modules as each of these modules requires a high voltage for operation. These modules 43, 45 are provided on a high-voltage portion 46 of the distributed printed circuit board 41. The controller module 47 and the communication module 49 can be considered low-voltage modules as each of these modules requires a low voltage for operation. These modules 47, 49 are provided on a low-voltage portion 48 of the distributed printed circuit board 41. The flexible members 55, 59, and 63 (or connectors) are positioned such that, when the distributed printed circuit board 41 is folded to be positioned within the external housing 3, as discussed in greater detail hereinafter, the spacing between the high-voltage modules and the low-voltage modules provides at least one of isolation of high-voltage from low-voltage or minimizes interference, such as electromagnetic interference, between the modules. The spacing provided between the high-voltage modules and the low-voltage modules is desirably at least 0.350 inches. In some embodiments, one or more of the members 55, 59, and 63 can include a flexible portion of the distributed printed circuit board 41. In some embodiments, one or more of the members 55, 59, and 63 can be a separate connector, for example, a wire, cable, flex connector such as a ZIF (zero insertion force) connector, or any suitable electrical connector known to those skilled in the art.

The first portion 51 of the distributed printed circuit board 41 that encompasses the discharge module 43 may be a long, narrow printed circuit board. It has a length in the range of about 4 to 6 inches and a width in the range of about 0.5 to 1.5 inches. This configuration of the first portion 51 allows it to be fit securely within a bottom portion of the external housing 3 substantially perpendicular to the front cover 7 and the rear cover 9. The first portion 51 of the distributed printed circuit board 41 comprises a plurality of high voltage switches 65, such as Insulated Gate Bipolar Transistors (IGBTs), Field Effect Transistors (FETs), transistors, or Metal-Oxide Semiconductor Field-Effect Transistors (MOS-FETs). Desirably, IGBTs are used as the high voltage switch. The discharge module 43 is configured to selectively deliver an energy pulse stored in the energy storage module 45 to the patient based on a signal from the controller module 47. The energy pulse is sent from the discharge module 43 through the port 5 to the therapy pads 103.

The second portion 53 of the distributed printed circuit board 41 that encompasses the energy storage module 45 is also a long, narrow printed circuit board. It has a length in the range of about 5 to 6 inches and a width in the range of about 0.5 to 1.5 inches. This configuration of the second portion 53 allows it to be fit securely within a bottom portion of the external housing 3 substantially perpendicular to the front cover 7 and the rear cover 9 and substantially parallel to the first portion 51. The second portion 53 of the distributed printed circuit board 41 includes a capacitive device mounted thereon, such as a bank of capacitors 67. Each of the capacitors in the bank of capacitors 67 may have a capacitance value of greater than 300 microfarads, such as 650 microfarads.

The second portion 53 further comprises the contact mechanism 233 for the battery pack 13 mounted thereon. The contact mechanism 233 is configured to extend through an opening 71 (see FIG. 4) provided within the battery well 15 of the external housing 3. The contact mechanism 233 is protected from the ingress of fluids by using an epoxy coating to seal off the underside of its blades. This allows the monitor unit 1 to be resistant to water or ingress of other materials into the interior of the external housing 3.

Figure 16:
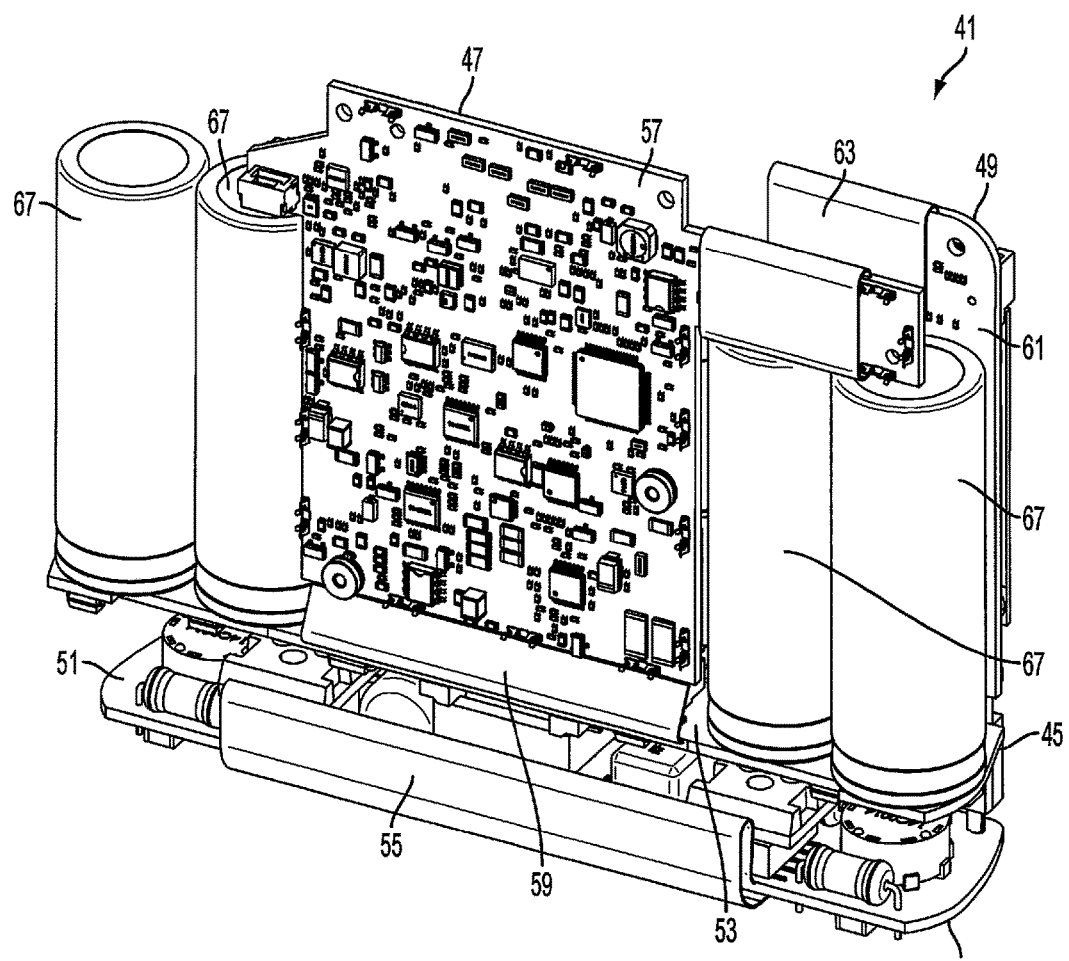
FIG. 16 is a rear perspective view of the distributed circuit board of FIG. 15.
Figure 17:
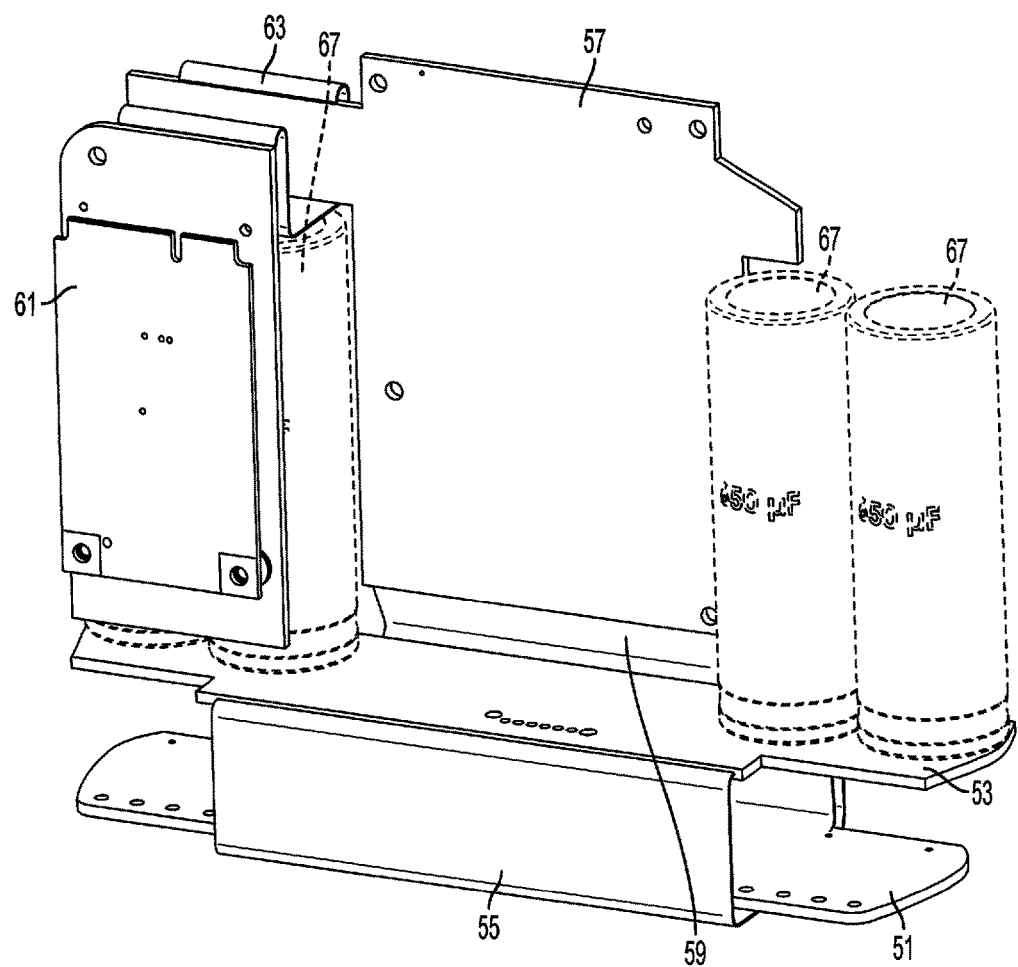
FIG. 17 is a front perspective view of the distributed circuit board of FIG. 15 with all of the electronic components removed from the portions of the circuit boards thereof.
Figure 18:
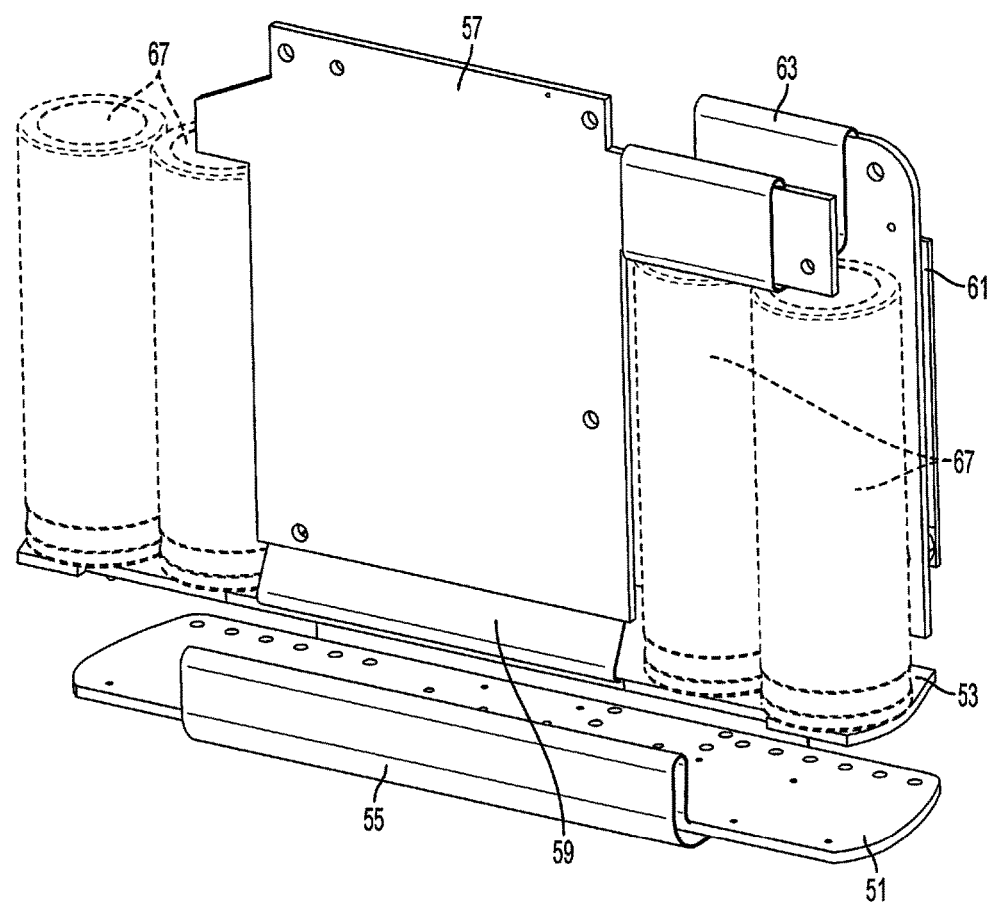
FIG. 18 is a rear perspective view of the distributed circuit board of FIG. 17.
Figure 19:
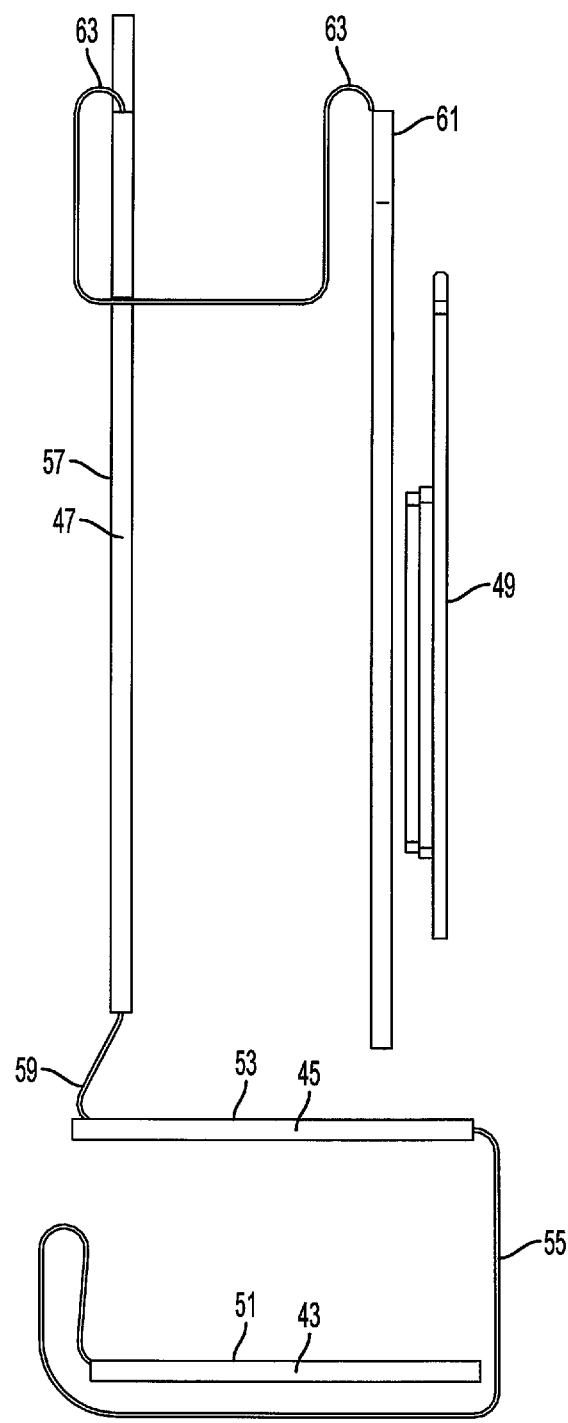
FIG. 19 is an end view of the distributed circuit board of FIG. 18.

The first flexible member 55 is folded such that the first portion 51 of the distributed printed circuit board 41 is positioned substantially parallel to the second portion 53 of the distributed printed circuit board 41. The first flexible member 55 has a sufficient length to prevent the first portion 51 from colliding with the second portion 53 when the distributed circuit board 41 is folded into the folded configuration (see FIGS. 15 and 16). Accordingly, the first flexible member 55 is folded such that it has a substantially C-shaped cross-section. With reference to FIGS. 17 and 18, all of the components have been removed from the distributed circuit boards 41 such that the manner in which the first flexible member 55 is folded can be more easily observed.

The third portion 57 of the distributed printed circuit board 41 that encompasses the controller module 47 generally has a length in the range of about 3.5 to 4.5 inches and a width in the range of about 2.5 to 3.5 inches. This configuration of the third portion 57 allows it to be fit securely within a central portion of the external housing 3 substantially parallel to the front cover 7 and the rear cover 9 and substantially perpendicular to the first portion 51 and the second portion 53. The second flexible member 59 extending between the second portion 53 and the third portion 57 of the distributed printed circuit board 41 is folded such that the third portion 57 is positioned substantially perpendicular to the first portion 51 and the second portion 53 of the distributed printed circuit board 41. The second flexible member 59 is folded such that it has a substantially L-shaped cross-section. With reference to FIGS. 17 and 18, all of the components have been removed from the distributed circuit boards such that the manner in which the second flexible member 59 is folded can be more easily observed.

The controller module 47 may comprise a microprocessor and memory device 75 and an SD card holder 77 mounted on a separate printed circuit board 79 that is operatively connected to the third portion 57 of the distributed printed circuit board 41. The memory device is desirably flash memory. These elements can be operatively connected to the separate printed circuit board 79 by ball grid arrays (BGAs) that are located so as to be minimally affected by mechanical stress that can be transmitted through the monitor unit 1, for example, such as upon impact of a portion of the housing of the monitor unit 1 with a hard surface. The BGAs can be located upon a separate printed circuit board 79 and/or upon a portion of the distributed printed circuit board 41 that is not susceptible to excess flexing, for example, on the third portion 57 of the distributed printed circuit board 41. If the BGAs that control the memory were placed indiscriminately on the distributed printed circuit board 41, they would be more susceptible to flexing, ultimately breaking the brittle solder balls that make up the base of the component. By moving the BGAs to the separate printed circuit board 79, or by selecting a portion of the distributed printed circuit board 41 that is not susceptible to excess flexing, for example, on the third portion 57 of the distributed printed circuit board 41, an extra layer of protection for the BGAs is provided since they are isolated from the bending of the distributed printed circuit board 41 during impacts or other mechanical loads, making the design more rugged, and increasing longevity.

The BGAs can be secured to the separate printed circuit board 79 or the third portion 57 of the distributed printed circuit board 41 by a suitable adhesive, for example, by being under-filled with an epoxy material, such as Loctite 3536 epoxy, available from Henkel AG & Co. KGaA of Dusseldorf, Germany. This process allows for the epoxy material to flow under the BGAs and around the solder balls that make the electro-mechanical connections to the separate printed circuit board 79 to form a rigid and secure support for the BGAs. Once under-filled, the BGAs are subjected to stress shielding, which further protects them from flexing.

Finally, finite element analysis (FEA) was utilized to estimate the flexure of the boards during drop simulations. To set up the analysis, a fixed boundary was established on the side of the external housing 3 impacting the ground, and then a 400G gravity load was applied to the system in the direction of a fall. This is a quasi-static estimation of a dynamic load, but is generally accurate for a 40 foot drop. Once the external housing 3 and distributed printed circuit board 41 are assembled, and the simulation run, the results of the analysis illustrated the area on third portion 57 of the distributed printed circuit board 41 where the BGAs of the separate printed circuit board 79 should be mounted (i.e., away from major flexure points in the distributed printed circuit board 41, which were centered around the screw holes). By mounting the separate printed circuit board 79 in this area, the BGAs thereof are prevented from failing due to flexure, thereby making the monitor unit 1 resistant to drop failures. The above-described measures allow the monitor unit 1 to be highly durable and resistant to breaking.

Furthermore, the separate printed circuit board 79 may be accessed and replaced, if needed, through an access opening 81 provided in a rear portion of the battery well 15 (see FIG. 4). This also allows a user to access an SD card from the SD card holder 77.

The microprocessor 75 is configured to receive digital or analog ECG information either directly or indirectly from the ECG electrodes (not shown) of the therapeutic device (not shown), detect abnormal heart rhythms based on the information received from the ECG electrodes, charge the capacitors 67 of the energy storage module 45, and control the energy discharge module 43 to administer a therapeutic shock to the patient, unless a user intervenes within a predetermined period of time via the response buttons 19. In at least one example, the predetermined period of time in which a user may intervene does not end until actual delivery of the therapeutic shock. An example of the methods used to detect abnormal heart rhythms can be found in U.S. Pat. No. 5,944,669, which is assigned to the assignee of the present application and which is hereby incorporated by reference in its entirety. Additionally, an example of the general features of a defibrillator can be found in U.S. Pat. No. 6,280,461, which is assigned to the assignee of the present application and which is also hereby incorporated by reference in its entirety.

The microprocessor 75 is also configured to perform several other functions. These other functions may leverage the robust computing platform provided by the microprocessor 75 without disrupting the therapy delivering functions of the monitor unit 1. Some examples of these other functions include notifying emergency personnel of the location of a patient who just received a therapeutic shock via the communication module 49, providing users of the device with the historical physiological data of the wearer of the device via the display screen 25, and/or notifying the manufacturer of the monitor unit 1 of potential performance issues within the monitor unit 1 that may require repair to or replacement of the monitor unit 1 via the communication module 49. Moreover, these other functions can include maintaining a history of data and events by storing this information in the memory device, communicating with the user via the display screen 25, and/or reporting data and events via the communication module 49. In addition, other functions may perform additional operations on the history of critical data. For instance, in one example, a function analyzes the history of critical data to predict worsening heart failure or an increased risk of sudden cardiac death.

The memory device of the monitor unit 1 is sized to store months or years of sensor information, such as ECG data, that is gathered over several monitoring and treatment periods. These monitoring and treatment periods may include continuous monitoring periods of approximately 23 hours (and substantially continuous monitoring periods of approximately 1-2 months) during which several treatments may be delivered to the patient. In some of these examples, the microprocessor 75 is configured to analyze the stored sensor information and to determine adjustments to the treatment method, or alternative treatment methods, of benefit to the patient. For instance, in one example, the microprocessor 75 is configured to analyze ECG data collected substantially contemporaneously with each instance of patient initiated delay, or cancellation of treatment. In this example, the microprocessor 75 is configured to analyze the stored months of ECG data to recognize individualized, idiosyncratic rhythms that, while not normal, do not indicate a need for treatment. In some examples, the microprocessor 75 may automatically adjust the treatment method of the monitor unit 1 to better suit the patient by not initiating treatment in response to the recognized, idiosyncratic rhythm. Such an adjustment may be performed in conjunction with review by appropriate medical personnel.

Figure 15:
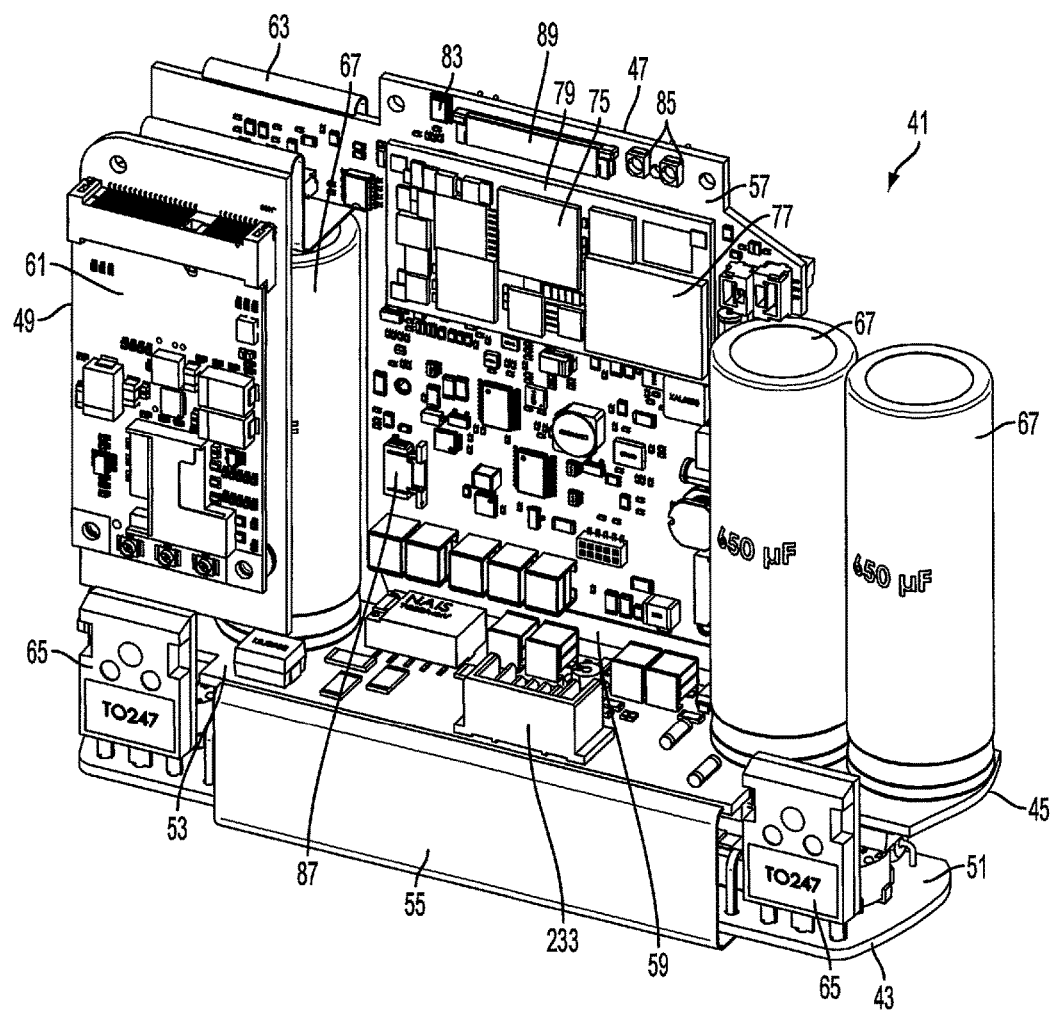
FIG. 15 is a front perspective view of the distributed circuit board of FIG. 13 in a folded configuration.

Referring now to FIG. 15, the third portion 57 of the distributed printed circuit board 41 may further comprise a microphone 83 mounted thereon. A silicon gasket (not shown) may be provided to direct the audio through the microphone port 23 provided on the exterior of the monitor unit 1 to the microphone 83.

In addition, a pair of LEDs 85 are mounted on the third portion 57 of the distributed printed circuit board 41. Light pipes can redirect the light from the LEDs 85 to a pair of lenses 86a, 86b provided on the top cover 11 of the monitor unit 1. In one embodiment, the LEDs 85 may be surface mounted to the distributed printed circuit board 41 such that they project perpendicular to the distributed printed circuit board 41, and the light pipes are used to bend the light to the pair of lenses 86a, 86b. In another embodiment, the LEDs 85 project parallel to the distributed printed circuit board 81 and the light pipes essentially shine straight through to the pair of lenses 86a, 86b. The LEDs 85 are configured as indication mechanisms to provide an indication to the patient of at least one condition of at least one of the defibrillator, the electrodes 101a, 101b, 101c, and 101d, the therapy pads 103, and the patient. The LEDs are viewable on the top cover 11 of the monitor unit 1 such that they are visible without manipulation of the device.

More specifically, the LED 85 visible through lens 86a may be a solid green indicator that provides an indication to the patient that the monitor unit 1 is active and operating properly. The LED 85 visible through lens 86b may be a flashing yellow indicator that is activated when a notification is displayed on the display screen 25. In some embodiments, the LED 85 visible through lens 86b providing the second flashing yellow indicator is activated only when a notification is displayed on the display screen 25.

These LEDs 85 provide a simple visual status indication to the patient while he/she is wearing the device. Multiple LEDs 85 and multiple color outputs by the LEDs 85 allow multiple status messages to be conveyed to patients during operation of the monitor unit 1. In one embodiment, two LEDs 85 are viable through lenses 86a, 86b provided on the top cover 11 of the monitor unit 1, thereby providing a first or green indicator 90 and a second or yellow indicator 92. When activated, one LED 85 is green 90 and the other is yellow 92. A third LED is provided under the response buttons 19 as described hereinabove such that it is viewable to the patient through at least the top surface 88 of at least one of the response buttons 19. Desirably, the third response button LED is red in color. In certain embodiments, the third LED is a set of LEDs, one associated with each of the buttons 19.

The following provides a brief description of the manner in which the three LEDs described hereinabove function as status indicators. Please note that this description is for exemplary purposes only and is not to be construed as limiting the invention as other systems may be utilized for providing status indicators using LEDs.

Initially, when the device is turned on both the green and yellow indicators 90, 92 are provided OFF, as is the response button LED. If the monitor unit 1 requires a test of the response buttons 19, the response button LED is provided in a solid ON fashion and the green and yellow indicators 90, 92 are both provided in a solid ON fashion as well. If a belt 111 (see FIG. 1) attaching the monitor unit 1 and/or the electrodes 101a, 101b, 101c, and 101d and therapy pads 103 to the patient are not connected properly, the green indicator 90 is provided OFF and the yellow indicator 92 is provided in a continuously flashing manner. A notification screen is provided on the display screen 25 to aid the user in determining the reason that the yellow indicator 92 is flashing.

The yellow indicator 92 remains flashing until the patient properly connects the belt 111 even if the display screen 25 times out and goes blank.

Once the belt 111 is properly connected and the monitor unit 1 is turned on and monitoring the patient, the green indicator 90 is provided in a solid ON fashion and the yellow indicator 92 is OFF. If during the monitoring, a notification appears on the display screen 25 of the monitor unit 1 (such as indicating that the belt 111 needs adjusted, batteries low, etc.), the green indicator 90 turns OFF and the yellow indicator 92 begins flashing. The yellow indicator 92 may flash at 0.4 Hz to 0.8 Hz with a 20% to 60% ON duty cycle. Once the patient acknowledges the notification screen (i.e., by pressing a button, providing a remedy to the problem, etc.), the yellow indicator 92 stops flashing and the green indicator turns 90 ON. Finally, when the patient is notified that an arrhythmia has been detected and a treatment is expected, the green indicator 90 turns OFF, the yellow indicator 92 turns OFF, and the response button LED begins flashing. The response button LED may flash at 1.4 Hz to 2.8 Hz with a 20% to 60% ON duty cycle.

Alternatively, the at least one indication mechanism may be a visual indication or audible indication. Such visual indications may be provided on a display screen, and may comprise a visual prompt, such as an instruction, a flashing screen, and the like. The audible indications may be provided by the speaker and may include audible prompts, such as instructions or sounds. If instructions are provided, such instructions may be automated instructions recorded on the monitor unit 1 or manual instructions provided by a person at a central monitoring station. Such indications may be coordinated with the LEDs 85.

A flex connector 87 for the touch screen of the display screen 25 and a flex connector 89 for the LCD of the display screen 25 can be mounted on the third portion 57 of the distributed printed circuit board 41. These connectors 87, 89 allow the display screen 25 to be operatively coupled to the third portion 57 of the distributed printed circuit board 41. Alternatively, one or more of the flex connectors 87, 89 can include a flexible portion of the distributed printed circuit board 41.

The fourth portion 61 of the distributed printed circuit board 41 that encompasses the communication module 49 may have a width that is greater than its length. Generally, it has a length in the range of about 0.5 to 1.5 inches and a width in the range of about 2.5 to 3.5 inches. This configuration of the fourth portion 61 allows it to be fit securely within the external housing 3 substantially parallel to the front cover 7 and the rear cover 9 and substantially perpendicular to the first portion 51 and the second portion 53. The third flexible member 63, extending between the third portion 57 and the fourth portion 61 of the distributed printed circuit board 41, is folded such that the fourth portion 61 is positioned substantially perpendicular to the first portion 51 and the second portion 53 of the distributed printed circuit board 41 and substantially parallel to the third portion 57 of the distributed printed circuit board 41. The third flexible member 63 is folded such that it has a substantially S-shaped cross-section, as shown in FIG. 9a.

The communication module 49 provided on the fourth portion 61 of the distributed printed circuit board 41 provides various devices for communicating information to and from the monitor unit 1. For instance, the communication module 49 may include a GPS transceiver, a Bluetooth™ transceiver, a Wi-Fi transceiver, and/or a cellular transceiver. The communication module 49 is controlled by the controller module 47 to communicate information regarding the monitor unit 1 as discussed hereinabove.

A cellular antenna (not shown) for the cellular transceiver can be positioned within the external housing 3 of the monitor unit 1. The cellular antenna is optimized to have peak efficiency at the cell frequencies of several regions including, but not limited to, the United States, Japan, and Europe. The cellular antenna is located under the dragon trail lens of the display screen 25 and far enough away from the distributed printed circuit board 41 so that it can communicate efficiently. As shown in FIG. 15, in some embodiments, a metallic portion of the third portion 57 of the distributed printed circuit board 41 functions as part of the cellular antenna. Alternatively, a metallic portion of the display screen 25 may function as part of the cellular antenna.

Similarly, an RFID antenna 91 (see FIGS. 10 and 11) may be positioned within the external housing 3 of the monitor unit 1 away from the four portions of the distributed printed circuit board 41 in order to communicate efficiently. In order to accommodate the RFID antenna 91, a backup battery 93 was positioned in the location shown in FIGS. 20 and 21. By positioning the RFID antenna 91 and the backup battery in this manner the effective range of the RFID antenna was maximized such the effective read range is about 9 inches. The RFID antenna 91 is used to quickly communicate the identification of the monitor unit 1 to service personnel. With reference to FIG. 22, a schematic diagram illustrating an RFID system utilized by the monitor unit 1 is described. The RFID system comprises an RFID module 300 comprising an RFID transceiver operatively coupled to the RFID antenna 91. The RFID module 300 is operatively coupled to the microprocessor and memory device 75 of the monitor unit 1.

The RFID module 300 is configured to have information written thereto and information read therefrom. Accordingly, the monitor unit 1 is capable of reading and writing information to the RFID module 300 from the microprocessor and memory device 75. In addition, an external device 302 that includes an RFID module 304 operatively coupled to an RFID antenna 306 and a microprocessor 308. The RFID module 300 of monitor unit 1 is configured to perform a variety of functions. As mentioned hereinabove, the RFID module 300 may be configured to communicate the identification of the monitor unit 1 to a personal computing device (acting as external device 302) of service personnel. In addition, the RFID module 300 may further be used as an aid when servicing the monitor unit by configuring the RFID module 300 to automatically record problems during patient field use. The RFID module 300 may then be scanned during service by the RFID module 304 of the personal computing device (acting as external device 302) of service personnel. During such a scan, the RFID module 300 of the monitor unit provides an indication/flag to the RFID module 304 of the personal computing device (acting as external device 302) of service personnel of the problems that occurred during patient field use.

In addition, an external data writing mechanism at a shipping location may communicate with the RFID module 300 of the monitor unit 1 to write information thereto, such as shipping boxes, software versions, board revisions, assembly revisions, etc. This information may be later verified by reading this information from the RFID module 300 using an external device 302 such as a personal computer.

A further example of the manner in which RFID module 300 of monitor unit 1 may be utilized to transmit and store information is the cloning of patient parameters from one monitor unit 1 to another. More specifically, in certain instances, it may be desirable to have patient parameters and information moved from one monitor unit 1 to another. The movement of such parameters and information may be accomplished utilizing the RFID module 300 as follows. First, the microprocessor and memory device 75 of a first monitor unit 1 writes its patient parameters into the RFID module 300. Thereafter, an external RFID reader (acting as external device 302) reads these patient parameters out of the RFID module 300 in the monitor unit 1. The external RFID reader then writes these patient parameters into an RFID module of a second monitor unit and the microprocessor and memory device 75 of the second monitor unit reads and stores these patient parameters and information from its RFID module, thereby cloning the patient parameters from one monitor to another.

Yet another use for RFID module 300 is in manufacturing to automatically configure the monitor unit 1 into a test mode so that it can be tested and/or initiate a self-test. More specifically, a monitor unit 1 may be returned to the manufacturer for servicing. At this time, testing of the monitoring unit is required. An external RFID reader (acting as external device 302) may be configured to write into the RFID module 300 of the monitor unit 1 a command to enter into a test mode or initiate a self-test. The microprocessor and memory device 75 of the monitor unit 1 then reads this information from the RFID module 300 and enters into the test mode or begins the self test.

While some uses for RFID module 300 of monitor unit 1 are discussed hereinabove, this list of uses is not to be considered as limiting the invention as other uses for RFID module 300 may also be incorporated into monitor unit 1.

Rather than using RFID, the present disclosure contemplates the use of other identification devices to achieve the above described objectives. For instance, the identification device may be any suitable storage device having reading and writing capabilities and wireless communication capabilities or wired communication capabilities. Examples of storage devices having wireless communication capabilities include, but are not limited to, a cellular-ready storage device, a Wi-Fi-ready storage device, and a short-range wireless communication protocol-ready storage device, such as a Bluetooth™-ready storage device. Examples of storage devices having wired communication capabilities include, but are not limited to, a flash drive, a USB device, a mini-USB device, a SD card, a miniSD card, a microSD card, and any other storage or memory device having a communication port for receiving a cable or bus.

Figure 13:
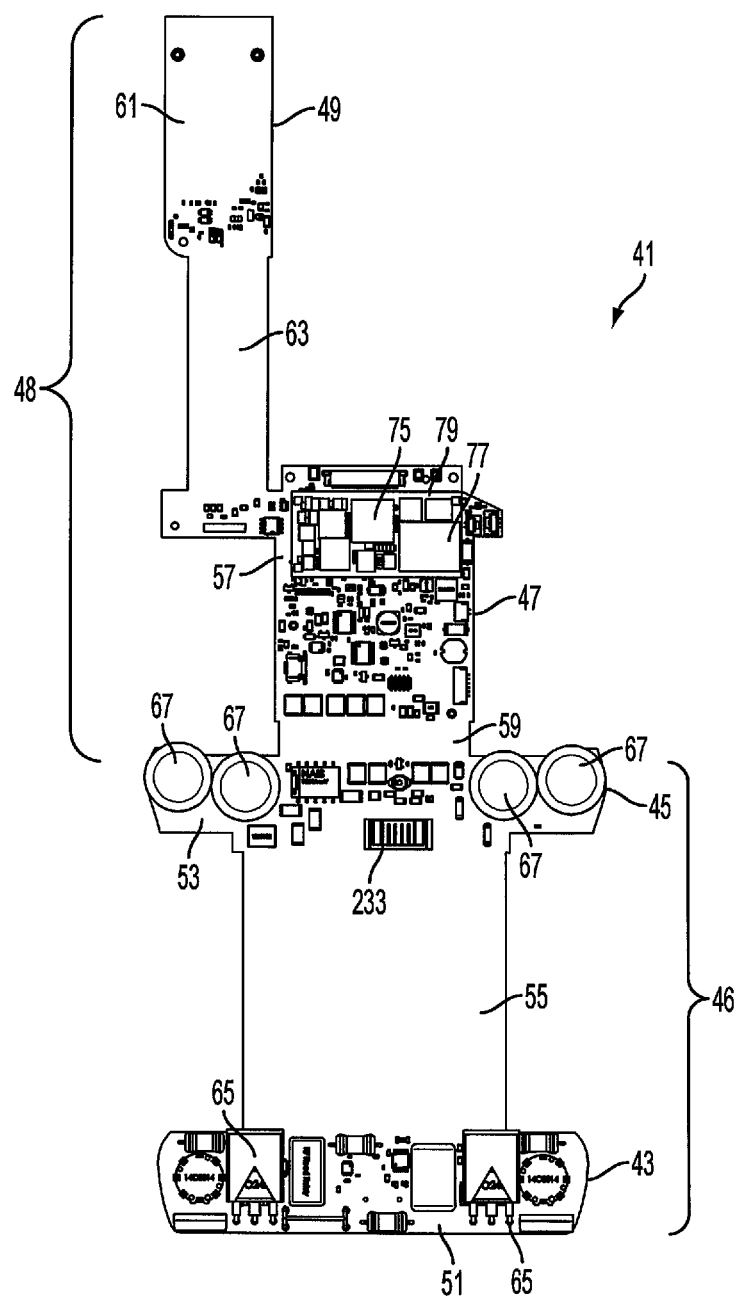
FIG. 13 is a top plan view of a distributed circuit board configured to be positioned within the housing of the monitor unit in accordance with the invention.
Figure 14:
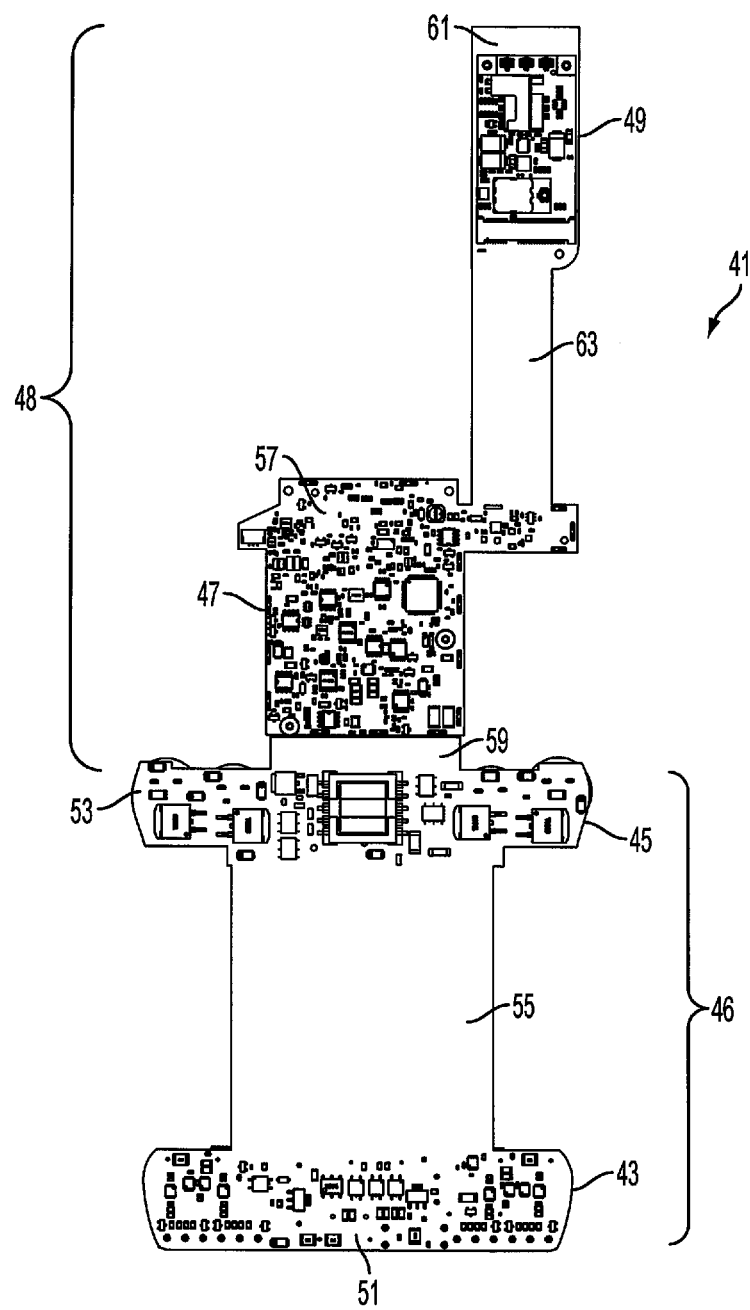
FIG. 14 is a bottom plan view of the distributed circuit board of FIG. 13.
Figure 20:
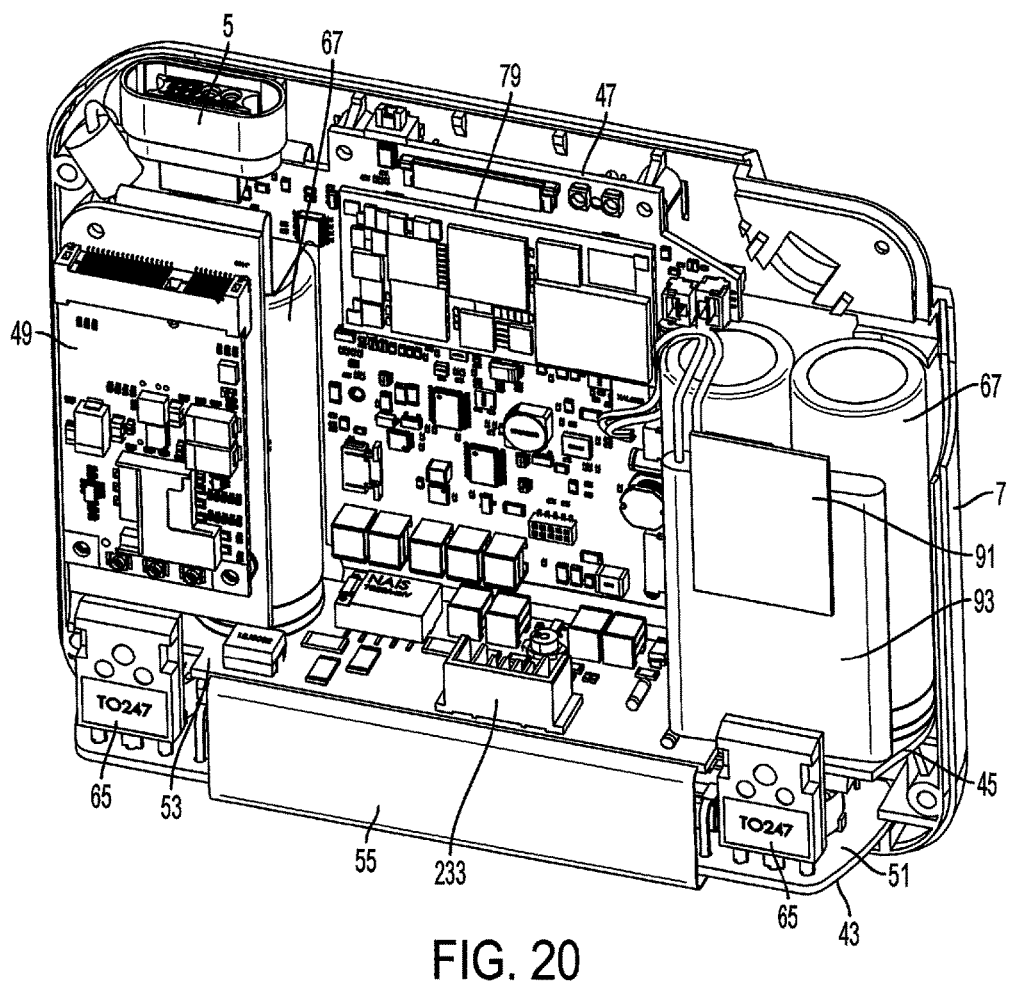
FIG. 20 is a front perspective view of the distributed circuit board of FIG. 15 positioned within a front cover plate of the external housing of FIG. 2.
Figure 21:
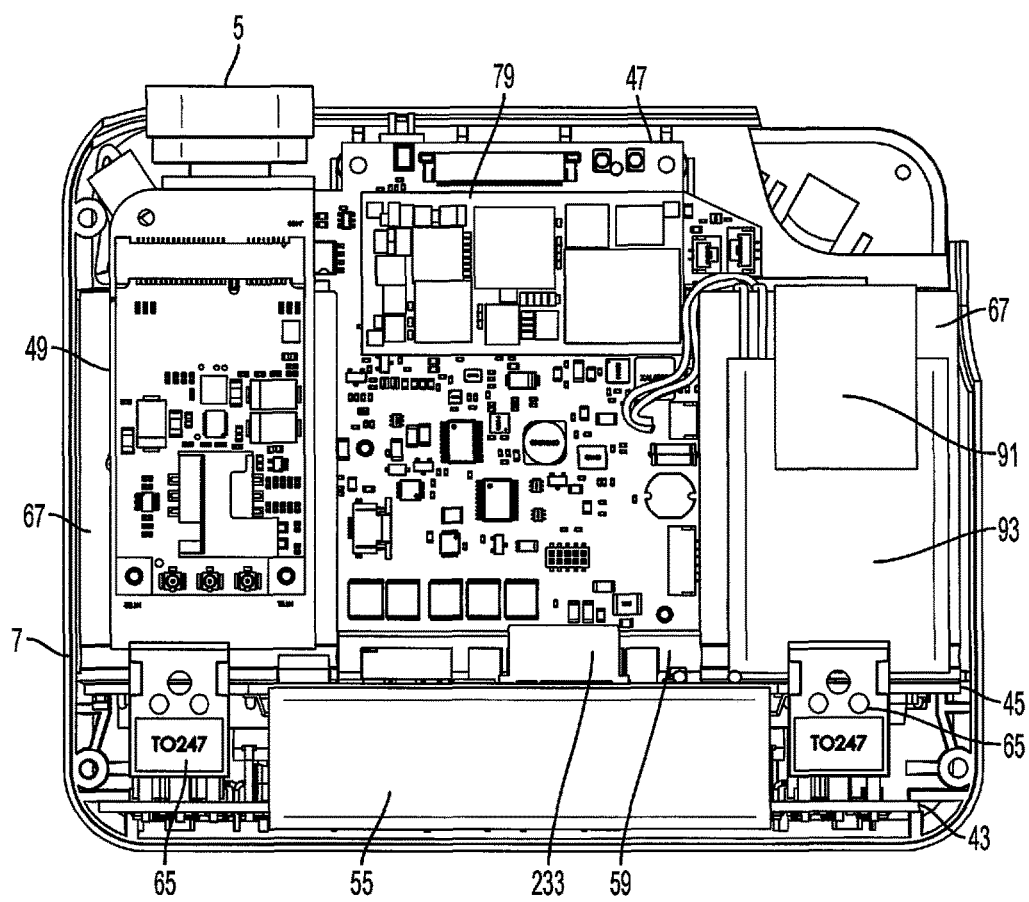
FIG. 21 is a front plan view of the distributed circuit board and housing of FIG. 20.
Figure 22:
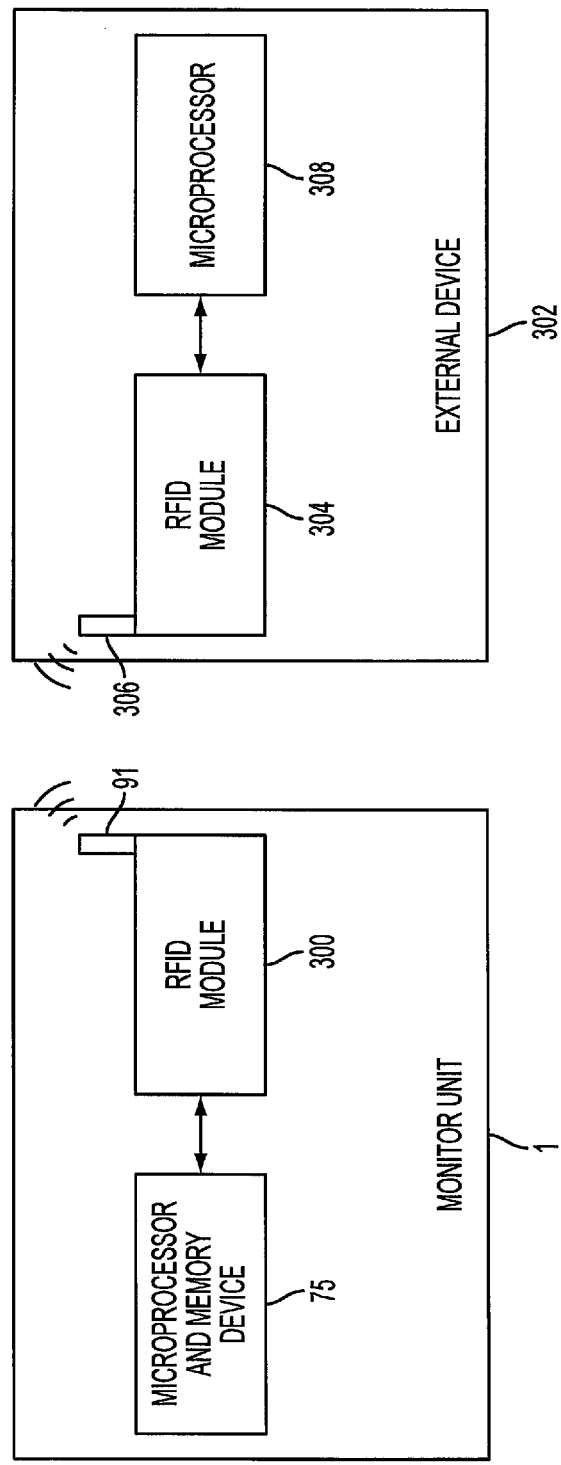
FIG. 22 is a schematic block diagram of an RFID module for use with the monitor unit of the defibrillator in accordance with the invention.

With reference to FIGS. 20 and 21 and with continuing reference to FIGS. 2-4 and 13-19, the monitor unit 1 may be manufactured as follows. First, the distributed printed circuit board 41 is provided in the unfolded configuration as shown in FIG. 13. Thereafter, the first flexible member 55 is folded such that the first portion 51 of the distributed printed circuit board 41 is positioned substantially parallel to the second portion 53 of the distributed printed circuit board 41. Next, the second flexible member 59 is folded such that the third portion 57 of the distributed printed circuit board 41 is positioned substantially perpendicular to the first and second portions 51, 53 of the distributed printed circuit board 41. Then, the third flexible connector 63 is folded such that the fourth portion 61 of the distributed printed circuit board 41 is positioned substantially parallel to the third portion 57 of the distributed printed circuit board 41 and substantially perpendicular to the first and second portions 51, 53 of the distributed printed circuit board 41, thereby providing a folded distributed circuit board as shown in FIGS. 15 and 16. When folded in this manner, the high voltage energy storage module 45 and discharge module 43 are isolated from the low voltage controller module 47 and communication module 49. In addition, by positioning the communication module 49 in this manner, interference between the components of the communication module 49 and other components of the device can be substantially avoided and eliminated.

Next, the front cover 7, rear cover 9, and top cover 11 are provided. The folded distributed printed circuit board 41 is positioned within the front cover 7 and secured thereto via an appropriate fastening device, such as screws. Finally, the top cover 11 is positioned in the appropriate location and the rear cover 9 is secured to the front cover 7 and top cover 11 using any appropriate fastening device. This produces a monitor unit 1 as shown in FIGS. 2 and 3.

Accordingly, a monitor unit 1 is provided that has a small footprint, is very durable, and can be used in a variety of patient care scenarios where a conventional implantable cardioverter-defibrillator cannot. Examples of these scenarios include treatment when the patient is awaiting a pending transplant or where the patient has a systemic infection (e.g., influenza or osteomyelitis), myocarditis, intra-ventricular thrombus, cancer, or a life-limiting serious illness such that an implantable device is not medically prudent.

Although a defibrillator 100 having a monitor unit 1 has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

The invention claimed is:

1. A wearable medical device configured to be worn by an ambulatory patient, comprising:

a defibrillator configured to deliver therapeutic shocks to the ambulatory patient; at least one sensor operatively connected to the defibrillator and configured to be worn by the ambulatory patient and monitor at least one physiological signal of the ambulatory patient;

one or more therapy pads operatively connected to the defibrillator and configured to administer the therapeutic shocks to the ambulatory patient;

a garment worn by the ambulatory patient and configured to support the at least one sensor and the one or more therapy pads;

at least one first identification device associated with the wearable medical device and configured to have device information read therefrom and written thereto; and at least one controller operatively connected to the at least one sensor and the at least one identification device and configured to at least one of retrieve the device information from the at least one identification device and write the device information to the at least one identification device, wherein the at least one first identification device is configured to be:

interrogated by at least one device positioned externally from the wearable medical device to obtain the device information from the at least one first identification device and write the device information to at least one second identification device; and provided with a command by the at least one device positioned externally from the wearable medical device to cause the at least one controller to enter into a test mode when the command is read from the at least one first identification device; and wherein the device information comprises at least one of patient parameters of the ambulatory patient wearing the wearable medical device, and self-test mode configuration.

2. The wearable medical device of claim 1, wherein the at least one first identification device is a radio frequency identification (RFID) module comprising at least an RFID transceiver and antenna.

3. The wearable medical device of claim 2, wherein the antenna is spaced from a backup battery within a housing of the wearable medical device.

4. The wearable medical device of claim 1,
wherein the at least one first identification device has information identifying the wearable medical device stored thereon, and
wherein the information identifying the wearable medical device is accessible by the at least one device positioned externally from the wearable medical device for identification of the wearable medical device thereby.

5. The wearable medical device of claim 1,
wherein the at least one controller is configured to record problems that occur with the wearable medical device during patient field use to the at least one first identification device; and
wherein the at least one first identification device is configured to be interrogated by the at least one device positioned externally from the wearable medical device to obtain the recorded problems for diagnosis by service personnel.

6. The wearable medical device of claim 1, wherein the device information comprises at least one of software versions, board revisions, and assembly revisions.

7. The wearable medical device of claim 1, wherein the at least one device positioned externally from the wearable medical device is an external RFID reader.

8. The wearable medical device of claim 1, wherein the at least one second identification device is associated with a second wearable medical device.

9. The wearable medical device of claim 8, wherein at least one controller of the second wearable medical device is configured to read the device information from the at least one second identification device and to store the patient parameters.

10. The wearable medical device of claim 1, wherein the at least one first identification device is a storage device having reading and writing capabilities and wireless communication capabilities.

11. The wearable medical device of claim 10, wherein the storage device comprises at least one of a cellular-ready storage device, a Wi-Fi-ready storage device, and a short-range wireless communication protocol-ready storage device.

12. The wearable medical device of claim 1, wherein the at least one first identification device is a storage device having reading and writing capabilities and wired communication capabilities.

13. The wearable medical device of claim 12, wherein the storage device comprises at least one of a flash drive, a USB device, a mini-USB device, a SD card, a miniSD card, and a microSD card.

14. The wearable medical device of claim 1, wherein the at least one sensor is configured to be worn by the ambulatory patient to continuously monitor the patient.

15. The wearable medical device of claim 14, wherein the at least one sensor continuously monitors the ambulatory patient for at least 24 hours.

16. A system comprising:
a first wearable medical device comprising:
a first defibrillator configured to deliver therapeutic shocks to an ambulatory patient;
at least one first sensor operatively connected to the first defibrillator and configured to be worn by the ambulatory patient and monitor at least one physiological signal of the ambulatory patient;
one or more first therapy pads operatively connected to the first defibrillator and configured to administer the therapeutic shocks to the ambulatory patient;
a first garment configured to be worn by the ambulatory patient and configured to support the at least one first sensor and the one or more first therapy pads;
a first identification device configured to have first device information and self-test configuration information read therefrom and written thereto, and
a first controller operatively connected to the first identification device and configured to write the first device information and self-test configuration information to the first identification device,
wherein the first identification device is configured to be interrogated to obtain the first device information and self-test configuration information;
a second wearable medical device, wherein the second wearable medical device is configured to be a clone of the first wearable medical device, the second wearable medical device comprising:
a second defibrillator configured to deliver therapeutic shocks to the ambulatory patient;
at least one second sensor operatively connected to the second defibrillator and configured to be worn by the ambulatory patient and monitor at least one physiological signal of the ambulatory patient;
one or more second therapy pads operatively connected to the second defibrillator and configured to administer the therapeutic shocks to the ambulatory patient;
a second garment configured to be worn by the ambulatory patient and configured to support the at least one second sensor and the one or more second therapy pads;
a second identification device configured to receive the first device information and self-test configuration information from the first identification device such that the first device information and self-test configuration information is written to the second identification device, and
a second controller operatively connected to the second identification device and configured to:
retrieve the first device information and self-test configuration information from the second identification device;
store the first device information and self-test configuration information in a memory operably connected to the second controller such that the retrieved first device information and self-test configuration information is cloned from the written first device information of the first wearable medical device; and operate the second wearable medical device in accordance with the retrieved first device information and self-test configuration information that is cloned from the written first device information and self-test configuration information of the first wearable medical device; and at least one device positioned externally from the first wearable medical device and the second wearable medical device to write into the first or second identification device a command to cause the corresponding first controller of the first wearable medical device or second controller of the second wearable medical device to enter into a test mode based on the command.

17. The system of claim 16, wherein the first identification device and the second identification device are RFID modules that each comprise at least an RFID transceiver and antenna.

\* \* \* \* \*

UNITED STATES PATENT AND TRADEMARK OFFICE
CERTIFICATE OF CORRECTION

PATENT NO. : 10,155,118 B2
APPLICATION NO. : 14/448761
DATED : December 18, 2018
INVENTOR(S) : Thomas E. Kaib et al.

Page 1 of 1

It is certified that error appears in the above-identified patent and that said Letters Patent is hereby corrected as shown below:

In the Claims

Column 18, Line 62, Claim 1, delete "be;" and insert -- be: --

Signed and Sealed this
Seventh Day of May, 2019

Andrei Iancu
*Director of the United States Patent and Trademark Office*